US009320580B2

(12) United States Patent
Montgomery

(10) Patent No.: US 9,320,580 B2
(45) Date of Patent: Apr. 26, 2016

(54) HAND-HELD TOOTH WHITENING INSTRUMENT WITH APPLICATOR RESERVOIR FOR WHITENING COMPOSITION AND METHODS OF USING SAME

(71) Applicant: Oraceutical LLC, Lee, MA (US)

(72) Inventor: R. Eric Montgomery, Monterey, MA (US)

(73) Assignee: Oraceutical LLC, Lee, MA (US)

( * ) Notice: Subject to any disclaimer, the term of this patent is extended or adjusted under 35 U.S.C. 154(b) by 0 days.

(21) Appl. No.: 13/867,091

(22) Filed: Apr. 21, 2013

(65) Prior Publication Data

US 2014/0315142 A1    Oct. 23, 2014

(51) Int. Cl.
*A61C 3/00*       (2006.01)
*A61C 19/06*      (2006.01)
(Continued)

(52) U.S. Cl.
CPC .............. *A61C 19/066* (2013.01); *A61C 17/005* (2013.01); *A61N 5/0603* (2013.01);
(Continued)

(58) Field of Classification Search
CPC .... A61C 19/06; A61C 19/063; A61C 19/066; A61C 17/005; A61N 5/062; A61N 2005/0606; A61N 2005/0651; A61N 5/0624; A61N 2005/0644; A61N 2005/0662; A61B 2018/00303; A61B 2018/00922
USPC ......... 433/29, 114–116, 215–216, 80, 89, 49, 433/163; 607/88–93; 206/368–369, 63.5, 206/209.1; 604/20, 290; 606/9; 401/183–186, 264
See application file for complete search history.

(56) References Cited

U.S. PATENT DOCUMENTS 3,235,459 A     2/1966  Francis
3,939,599 A *   2/1976  Henry et al. ................... 433/99
(Continued)

FOREIGN PATENT DOCUMENTS

EP      1262172     12/2002
WO      0226196     4/2002
(Continued)

OTHER PUBLICATIONS

Paris et al., "Penetration Coefficients of Commercially Available and Experimental Composites Intended to Infiltrate Enamel Carious Lesions", Dental Materials 23 (2007), pp. 742-748.
(Continued)

*Primary Examiner* — Heidi M Eide
(74) *Attorney, Agent, or Firm* — David M. Quinlan, P.C.

(57) ABSTRACT

A hand-held, ergonomic instrument with an LED that emits actinic light in visible wavelengths mounts a replaceable applicator cup with a reservoir for a tooth whitening composition held in place against a user's tooth during a whitening procedure. Actinic light is directed onto the tooth surface through a window in the cup and the tooth whitening composition substantially without attenuation, delivering at least about 100 milliwatts per square centimeter of light energy to the tooth surface. The cup includes a rigid body for mounting the cup to the instrument and an opaque flexible sleeve molded in place over the outside of the body to form a seal with the tooth surface and prevent exposure of soft mouth surfaces to the actinic radiation during a whitening procedure. A safety switch disables the LED when the applicator cup is not in contact with a tooth surface.

21 Claims, 5 Drawing Sheets

(51) Int. Cl.
*A61C 17/00* (2006.01)
*A61N 5/06* (2006.01)
*A61B 18/00* (2006.01)
*A61B 19/00* (2006.01)

(52) U.S. Cl.
CPC ..... *A61N5/0624* (2013.01); *A61B 2018/00303* (2013.01); *A61B 2018/00922* (2013.01); *A61B 2019/465* (2013.01); *A61N 5/062* (2013.01); *A61N 2005/0606* (2013.01); *A61N 2005/0644* (2013.01); *A61N 2005/0651* (2013.01); *A61N 2005/0662* (2013.01)

(56) References Cited

U.S. PATENT DOCUMENTS

| | | | |
|---|---|---|---|
| 4,661,070 | A | 4/1987 | Friedman |
| 4,952,143 | A | 8/1990 | Becker et al. |
| 5,004,124 | A | 4/1991 | Stefaniak et al. |
| 5,032,178 | A | 7/1991 | Cornell |
| 5,240,415 | A | 8/1993 | Haynie |
| 5,247,218 | A | 9/1993 | Sven |
| 5,401,495 | A | 3/1995 | Murayama |
| 5,658,148 | A | 8/1997 | Neuberger et al. |
| 5,785,527 | A | 7/1998 | Jensen et al. |
| 5,847,120 | A | 12/1998 | Collins et al. |
| 5,853,428 | A | 12/1998 | Collins et al. |
| 5,876,625 | A | 3/1999 | Collins et al. |
| 5,921,251 | A | 7/1999 | Joshi |
| 5,922,307 | A | 7/1999 | Montgomery |
| 5,938,439 | A | 8/1999 | Mertins et al. |
| 6,011,152 | A | 1/2000 | Gordon-Wylie et al. |
| 6,018,840 | A | 2/2000 | Guay et al. |
| 6,048,202 | A | 4/2000 | Jensen et al. |
| 6,051,704 | A | 4/2000 | Gordon-Wylie et al. |
| 6,054,580 | A | 4/2000 | Collins et al. |
| 6,056,548 | A | 5/2000 | Neuberger et al. |
| 6,099,586 | A | 8/2000 | Collins et al. |
| 6,100,394 | A | 8/2000 | Collins et al. |
| 6,136,223 | A | 10/2000 | Collins et al. |
| 6,164,967 | A | 12/2000 | Sale et al. |
| 6,174,516 | B1 | 1/2001 | Curtis et al. |
| 6,241,779 | B1 | 6/2001 | Collins et al. |
| 6,331,291 | B1 | 12/2001 | Glace et al. |
| 6,397,424 | B1 | 6/2002 | Leung |
| 6,521,215 | B2 | 2/2003 | Okay |
| 6,599,126 | B1 | 7/2003 | Sale et al. |
| 6,602,073 | B2 | 8/2003 | Schilling et al. |
| 6,611,110 | B1* | 8/2003 | Fregoso ........................ 315/224 |
| 6,623,272 | B2 | 9/2003 | Clemans |
| 6,759,030 | B2 | 7/2004 | Kosti |
| 6,792,640 | B2* | 9/2004 | Lev ................................. 15/28 |
| 6,800,671 | B1 | 10/2004 | Montgomery |
| 6,902,397 | B2 | 6/2005 | Farrell et al. |
| 7,060,818 | B2 | 6/2006 | Horwitz et al. |
| 7,354,448 | B2 | 4/2008 | Altshuler et al. |
| 7,581,864 | B2 | 9/2009 | Craig |
| 8,002,546 | B2* | 8/2011 | Viscomi ........................ 433/141 |
| 8,033,746 | B2 | 10/2011 | Tsai |
| 8,177,450 | B2 | 5/2012 | Zhang |
| 8,214,958 | B2 | 7/2012 | Pinyayev et al. |
| 2001/0046477 | A1 | 11/2001 | Wolfe |
| 2003/0171702 | A1 | 9/2003 | Thompson et al. |
| 2004/0019990 | A1 | 2/2004 | Farrell et al. |
| 2004/0033205 | A1 | 2/2004 | Date et al. |
| 2004/0063075 | A1 | 4/2004 | Karazivan |
| 2004/0105834 | A1 | 6/2004 | Singh et al. |
| 2005/0026103 | A1 | 2/2005 | Wasylucha |
| 2005/0084826 | A1 | 4/2005 | Pilaro et al. |
| 2005/0175956 | A1 | 8/2005 | Russell et al. |
| 2005/0260142 | A1 | 11/2005 | Philp, Jr. et al. |
| 2006/0047329 | A1 | 3/2006 | Krespi et al. |
| 2006/0105292 | A1 | 5/2006 | Dorsey et al. |
| 2006/0183081 | A1 | 8/2006 | Bevilacqua et al. |
| 2006/0198795 | A1 | 9/2006 | Giniger |
| 2006/0198797 | A1 | 9/2006 | Giniger |
| 2006/0223024 | A1 | 10/2006 | Hochman |
| 2006/0240386 | A1 | 10/2006 | Yaniv et al. |
| 2006/0264532 | A1 | 11/2006 | Meyer-Luckel et al. |
| 2007/0092455 | A1 | 4/2007 | Harwood |
| 2007/0098483 | A1 | 5/2007 | Milesi et al. |
| 2007/0105063 | A1 | 5/2007 | Pinyayev et al. |
| 2007/0160958 | A1 | 7/2007 | Belikov et al. |
| 2007/0237727 | A1 | 10/2007 | Matthews |
| 2007/0271714 | A1* | 11/2007 | Adam et al. .................. 15/22.2 |
| 2007/0298369 | A1 | 12/2007 | Rizoiu et al. |
| 2008/0057463 | A1* | 3/2008 | Wong et al. .................... 433/29 |
| 2008/0060148 | A1 | 3/2008 | Pinyaev et al. |
| 2008/0131834 | A1 | 6/2008 | Shepherd et al. |
| 2008/0206706 | A1 | 8/2008 | Mossle |
| 2008/0213731 | A1 | 9/2008 | Fishbourne |
| 2008/0255549 | A1 | 10/2008 | Rose et al. |
| 2008/0256729 | A1 | 10/2008 | Link |
| 2008/0274066 | A1 | 11/2008 | Montgomery |
| 2008/0274442 | A1 | 11/2008 | Klee et al. |
| 2008/0286713 | A1 | 11/2008 | Nanda |
| 2009/0081605 | A1* | 3/2009 | Hay et al. ........................ 433/29 |
| 2009/0092563 | A1 | 4/2009 | Allred et al. |
| 2009/0271936 | A1 | 11/2009 | Walanski et al. |
| 2011/0123958 | A1* | 5/2011 | Piergallini et al. ......... 433/217.1 |
| 2011/0144010 | A1 | 6/2011 | Kennedy |
| 2011/0256501 | A1 | 10/2011 | Lampert |
| 2012/0258418 | A1 | 10/2012 | Shen |
| 2013/0164710 | A1 | 6/2013 | Montgomery |
| 2014/0113253 | A1 | 4/2014 | Montgomery |

FOREIGN PATENT DOCUMENTS

| | | |
|---|---|---|
| WO | 2004103303 | 12/2004 |
| WO | 2005041911 | 5/2005 |
| WO | 2005072692 | 8/2005 |
| WO | 2011133793 | 10/2011 |

OTHER PUBLICATIONS

Cadenaro et al., "Influence of Whitening on the Degree of Conversion of Dental Adhesives on Dentin," Eur. J. Oral Sci., vol. 114 (2006), pp. 257-262.

Kugel et al., "Composites and Whitening: How and When to Combine Treatments," http://www.dentalaegis.com/special-issues/2007/03/composites-and-whitening-how-and-when-to-combine-treatments (last visited Jul. 19, 2013).

International Preliminary Report on Patentability and Written Opinion in PCT/US2011/033464, Aug. 15, 2013.

* cited by examiner

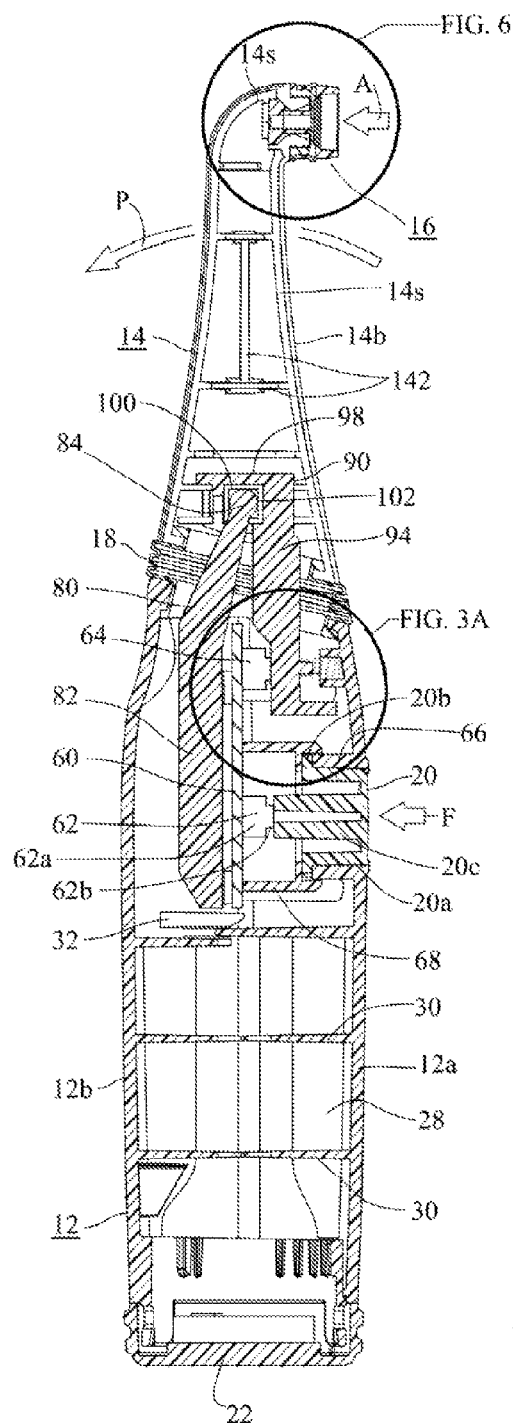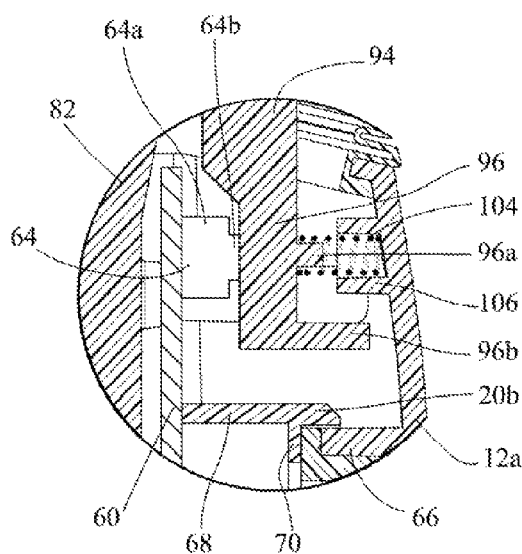
FIG. 3A
FIG. 3

HAND-HELD TOOTH WHITENING INSTRUMENT WITH APPLICATOR RESERVOIR FOR WHITENING COMPOSITION AND METHODS OF USING SAME

BACKGROUND OF THE INVENTION

1. Field of the Invention

The present invention relates to a hand-held device for whitening teeth, and more particularly, to such a device that has an actinic light applying tip with a reservoir for directly contacting a user's teeth with a whitening composition through which the actinic light passes.

2. Background of Invention and Related Art

Teeth can become discolored by chromogenic (color-causing) substances in food, beverages, tobacco, and salivary fluid, in addition to blood, amalgam restoratives, and antibiotics such as tetracycline. Tooth structures generally responsible for presenting a stained appearance are enamel, dentin, and the acquired pellicle. Tooth enamel is predominantly inorganic, mostly in the form of hydroxyapatite crystals, but it also contains approximately 5% organic material primarily in the form of collagen. Dentin is composed of about 20% protein including collagen, the balance consisting of inorganic material, predominantly hydroxyapatite crystals similar to those found in tooth enamel. The acquired pellicle is a proteinaceous layer on the surface of tooth enamel which re-forms rapidly after an intensive tooth cleaning.

Tooth stains may be either extrinsic or intrinsic, depending upon their location within the tooth structure. For example, extrinsic staining, of the acquired pellicle, arises as a result of compounds such as tannins and other polyphenolic compounds which become trapped in and tightly bound to the proteinaceous pellicle layer that spontaneously forms on the surface of the teeth. This type of staining can usually be removed by mechanical methods of tooth cleaning that remove all or part of the acquired pellicle together with the associated stain. On the other hand, intrinsic staining, of the enamel and/or dentin, can occur when chromogens or pre-chromogens penetrate and become tightly bound to these tooth structures. Intrinsic staining may also arise from systemic sources of chromogens or pre-chromogens, such as excess fluoride intake during enamel development, which can lead to the mottled yellow or brown spots typical of fluorosis staining. Intrinsic staining by its nature is not amenable to mechanical methods of tooth cleaning and generally requires the use of chemicals, such as hydrogen peroxide, that can penetrate into the tooth structure, in order to effect a change in the light absorptivity of the chromogens bound there. In general, intrinsic staining is more intractable and difficult to remove than extrinsic staining.

Given these two basic types of tooth staining, tooth cleaning approaches generally fall into two categories. One comprises the mechanical agitation of gels, pastes, or liquids, including toothpastes, at the tooth surface to effect extrinsic stain removal through abrasive erosion of the stained acquired pellicle. The other, particularly adapted for mitigating intrinsic staining, comprises contacting the tooth with a formulation typically comprising a gel, paste, or liquid that accomplishes a chemical bleaching effect while in contact with the stained tooth surface for a specified period (with or without the application of mechanical cleaning action), after which the formulation is removed. In some cases, an auxiliary chemical process or additive, which may be oxidative or enzymatic, supplements the mechanical process.

The most effective bleaching compositions contain an oxidizing agent, such as hydrogen peroxide, that attacks the bound chromogen molecules in such a way as to render them colorless, water-soluble, or both. In one popular approach a dental professional constructs a custom-made tooth-bleaching tray for the patient from an impression of the patient's dentition. On his or her own, the patient dispenses a prescribed oxidizing gel into the tooth-bleaching tray and wears it repeatedly for several minutes or hours at a time over a period ranging from about two weeks to six months, depending upon the severity of tooth staining. These oxidizing compositions, usually packaged in small plastic syringes, are dispensed directly by the patient into the custom tooth-bleaching tray and held in place in the mouth typically for an hour or more, sometimes up to eight to 12 hours in certain treatment regimens. The slow rate of bleaching is in large part the consequence of the very nature of the formulations that have been developed to maintain stability of the oxidizing composition. The most commonly used oxidizing compositions contain the hydrogen peroxide precursor carbamide peroxide mixed with an anhydrous or low water content, hygroscopic viscous carrier containing glycerin and/or propylene glycol and/or polyethylene glycol. When contacted by water, carbamide peroxide dissociates into urea and hydrogen peroxide. The slow rate of bleaching in this prior approach using a hygroscopic carrier has proven to cause tooth sensitization in over 50% of patients. This tooth sensitivity is believed to result from the movement of fluid through the dentinal tubules, which is sensed by nerve endings in the tooth. Worse, the carriers for the carbamide peroxide enhance this movement. In fact, it has been determined that glycerin, propylene glycol, and polyethylene glycol all can give rise to varying amounts of tooth sensitivity following exposure of the teeth to heat, cold, overly sweet substances, and other causative agents.

This kind of prolonged exposure of teeth to bleaching compositions has a number of other adverse effects in addition to causing tooth sensitivity. These include: solubilization of calcium from the enamel layer at a pH less than 5.5, with associated demineralization of the enamel; penetration of the intact enamel and dentin by the bleaching agents, which if they reach the pulp chamber of a vital tooth risk damage to pulpal tissue; and dilution of the bleaching composition with saliva, resulting in leaching of the composition from the dental tray and subsequent ingestion by the patient, not to mention reducing the efficacy of the bleaching process.

An alternate approach uses oxidizing compositions (generally with relatively high concentrations of oxidizers) that are applied directly to the tooth surface of a patient in a dental office under the supervision of a dentist or dental hygienist. Theoretically, such tooth whitening strategies have the advantage of yielding faster results and better overall patient satisfaction; however, due to the high concentration of oxidizing agents contained in these so-called "in-office" or "chairside" compositions, they can be hazardous to the patient and practitioner alike if not handled with care. The patient's soft tissues (the gingiva, lips, and other mucosal surfaces) must first be isolated from potential exposure to the active oxidizing agent by the use of a perforated rubber sheet (known as a rubber dam), through which only the teeth protrude. Alternatively, the soft tissue may be isolated from the oxidizers to be used in the whitening process by covering the tissue with a polymerizable composition that is shaped to conform to the gingival contours and subsequently cured by exposure to a high intensity light source. Applying these rubber dams and polymerizable compositions typically requires significant skill on the part of the clinician and can take up to 20 minutes.

Once the soft tissue has been isolated and protected, the practitioner applies the oxidizing agent directly onto the stained tooth surfaces for a specified period of time or until a sufficient change in tooth color has occurred, sometimes applying heat to enhance the bleaching action of the oxidizing composition. This approach yields satisfactory results, typically producing between five to nine shades of improvement in tooth whiteness (as measured with the VITA® Shade Guide, VITA Zahnfarbik, Bad Sackingen, Germany).

The VITA® Shade Guide used as standard for measuring tooth whiteness assigns shades from very light (B1) to very dark (C4). A total of 16 VITA® shades constitutes the entire range of colors between these two endpoints on a scale of brightness, and tooth whitening is often judged by the number of shade changes achieved. Professional whitening procedures can in some cases achieve a brightness increase of four or five VITA® shades, but a change as small as one to two shades will be noticed by most patients. Accordingly, the improvement of five to nine shades using the approach discussed in the previous paragraph can be considered a good result, but the procedure is time-consuming because it involves so many complicated steps, is expensive and inconvenient because it can only be performed by a dental professional in an office setting, and can be dangerous if it includes the application of heat (for reasons discussed in more detail below). Since most patients can notice a change of only one or two VITA® shades, many individuals would accept simpler, cheaper, more convenient, and safer alternatives, even if they did not improve tooth brightness as much as procedures using chairside compositions requiring professional application.

It is known that applying actinic radiation such as heat (infrared), discussed above, to the teeth during bleaching, particularly when the bleaching composition is a peroxide, speeds and enhances the whitening process. "Actinic radiation" refers to light energy capable of being absorbed by a tooth stain chromogen, or capable of accelerating the oxidation of a tooth stain chromogen in the presence of an oxidizing agent. The term actinic radiation may also mean light energy capable of accelerating chemical reactions in general. The terms "actinic radiation" and "actinic light" may be used interchangeably in this description. Known procedures involve the application of actinic light in ultraviolet and/or infrared wavelengths. Again, such methods can be effective for whitening teeth, but ultraviolet light can be hazardous to the patient and practitioner alike and infrared radiation may damage tooth structures and/or burn the patient unless precautions are taken.

U.S. Pat. No. 4,952,143 attempts to address these drawbacks with a dental bleaching instrument for use by a professional that filters out ultraviolet wavelengths and has a temperature regulation mechanism that involves placing a temperature sensor at the tooth surface to provide a feedback control mechanism to prevent excessive temperatures. However, that does not solve the basic problem that using heat at all can risk tooth damage, which means that this approach can be used only under the close supervision of a professional with the proper equipment. Even then, it still poses risks to tooth structures, especially in patients whose teeth may be prone to damage from heat.

A related technique is discussed in U.S. Pat. No. 5,032,178, which discloses compositions and methods that purportedly improve tooth whitening efficacy by using exposure to optical energy in the visible spectrum wavelength range of 400 to 700 nanometers. The compositions disclosed in this patent require the use of an aqueous solution of hydrogen peroxide with (1) an inert silica gelling agent, (2) a catalytic accelerator (either manganese sulfate monohydrate or ferrous sulfate), (3) an agent for providing thixoplasticity and thickening properties to the composition, such as cellulose ethers and methyl vinyl ethers, and (4) a redox color indicator, which indicates completion of the bleaching treatment of the teeth by transforming from one color to another in response to the dissociation of hydrogen peroxide over a given time period. The described compositions are combined into a homogeneous mixture prior to use with all of the required components dispersed evenly throughout the mixture. The compositions are not particularly transparent to light energy in the range of 400 to 700 nm because the inorganic silica particles inhibit light energy from reaching the tooth surface where it can act to sensitize chromogens in the tooth structures to the oxidizers in the mixture. Indeed, commercial mixtures based on this patent (available under the trade name Shofu Hi-Lite® from Shofu Dental Corporation, Menlo Park, Calif.) are nearly opaque. Typical results obtained using such compositions and methods are about two to three VITA® shades improvement in tooth color, similar to that achieved with compositions that do not employ light energy in the process of bleaching teeth. Thus, even though this approach uses visible light instead of ultraviolet or infrared radiation, the light seems to have little effect, and the procedure must be done by a dental professional.

A commercial product called Opalescence® Xtra® available for bleaching teeth in the controlled environment of a dental office has been introduced by Ultradent Products, Inc., South Jordan, Utah. U.S. Pat. No. 5,785,527 is believed to describe this product. The commercial product is supplied in a plastic syringe and is described in accompanying literature as a light-activated tooth whitening gel, which contains approximately 35% hydrogen peroxide. A pH determination showed the product to have a neat pH of about 4.0 at 25° C. The product is thickened to a loose, gel-like consistency with a polymer. Additionally, the product as sold, and as described in U.S. Pat. No. 5,785,527, contains a bright orange pigment or dye (carotene), claimed to be a photosensitizer that absorbs light energy and converts it to heat, thereby increasing the activity of the peroxide as a tooth bleaching agent. Indeed, the presence of a photoabsorber renders the composition relatively opaque to visible light at wavelengths from about 400 to 700 nm, which thus would not reach the tooth surface in a meaningful amount. Comparative clinical results show an improvement in tooth color of from about three to four VITA® shades, which is significant, but appears to depend more on the time of the composition remains in contact with the tooth surface, rather than any particular light or heat activation regimen. In addition, the low pH of the commercial product may cause a reduction in the microhardness of tooth enamel, due to the dissolution of hydroxyapatite crystals (which can occur at a pH of around 5.5 or less).

Devices for use in light/heat-activated tooth whitening procedures also include the commercially available Union Broach® Illuminator System, from Union Broach, a Health/Chem. Company. New York. N.Y. This device, as described by the manufacturer, provides direct, full spectrum illumination to all of the teeth found in the front of the average adult's mouth. The Union Broach light is used in conjunction with a 35% hydrogen peroxide solution (Superoxol), which requires a dental professional to apply to the teeth prior to and during illumination with the light source. However, this device does not uniformly illuminate all sixteen central teeth in the front upper and lower arches because of the curvature of the dentition. This potentially gives rise to uneven results. In addition, the Union Broach device generates a great deal of heat which is both uncomfortable for the patient and potentially damaging to the teeth, as already mentioned.

Commercially available professional teeth whitening devices that successfully and safely use light to enhance the removal of teeth stains are available. Most of these professional devices are LED projector-type tooth whitening devices which are designed to project high intensity actinic light from an emitting surface, typically an array of LEDs or other optical outputs. Professional light emitting devices typically emit in excess of 100 milliwatts per square centimeter of actinic light. Examples of successful professional tooth whitening devices include the Zoom® In-Office Whitening Lamp and the BriteSmile® whitening device (both sold by Discus Dental LLC, a division of Philips Oral Healthcare, Los Angeles, Calif.). These devices are maneuvered by the professional such that when positioned inside or just outside the mouth of the patient in close proximity to tooth surfaces, all of the "smile-line" teeth (8-10 uppers and 8-10 lowers) are exposed to actinic light at the same time. Since projector-type tooth whitening devices illuminate all of the patient's teeth and gum surfaces simultaneously, the soft tissues must be isolated and protected from exposure to the high intensity light to prevent possible damage. Typical isolation materials, such as those described in U.S. Pat. No. 6,048,202 and U.S. Pat. No. 6,800,671, are applied in liquid, gel, or paste form and subsequently polymerized to form the necessary isolation barrier before the tooth whitening procedure and exposure to light can begin. This can be a time-consuming and uncomfortable process for the patient.

These and other prior art tooth whitening devices and methods that use actinic radiation are all somewhat inconvenient to use because they require the intervention of a professional. They also demonstrate varying degrees of efficacy and safety, and in some cases can actually harm the teeth and soft tissues of the mouth if the professional using them fails to adhere strictly to proper procedures designed to prevent such damage. As a result, an effective manner of chemical tooth bleaching, that safely and effectively employs the enhancing action of actinic radiation in a form that presents a lesser risk of tooth damage and that does not require the involvement of a professional, would be highly advantageous.

The prior art does disclose some hand-held tooth whitening devices that apply actinic radiation and are designed for consumer use. Some examples are U.S. Pat. No. 6,056,548 and, more recently, Patent Pub. No. US2005/0026103 and No. US2011/0123958. The latter has an applicator head with a reservoir for a photoactivatable composition, and the reservoir has a cover through which the composition is extruded onto a treatment surface or, for its tooth bleaching embodiment, an absorbent pad such as a sponge in the reservoir holds the composition and is used to rub the tooth surface. Actinic radiation, produced by an LED, must pass through the sponge containing the photoactivatable composition.

While Patent Pub. No. US2011/0123958 describes a hand-held device meant to use actinic radiation for tooth whitening, the efficacy of the device as disclosed may be compromised by a number of factors. For one thing, the amount of actinic radiation available at the tooth surface will inevitably be attenuated by the sponge, and the photoactivatable composition absorbed in the sponge will by definition absorb actinic radiation passing through it and thus even further reduce the amount of radiation actually reaching the tooth surface. Even so, there may still be sufficient energy to present a hazard if the user inadvertently directs the light from the LED at his or her eye while using the device. Nor does there appear to be any mechanism for preventing exposure of soft tissues in the user's mouth from stray actinic radiation.

Home-use devices for applying actinic light in conjunction with tooth whitening compositions are commercially available in the form of actinic light emitting mouthpieces and projectors to illuminate all of the smile-line teeth at the same time. A serious drawback to these products is their inability to achieve levels of light intensity at the tooth surface during use required to accelerate the elimination of tooth stains because to do so would expose surrounding soft tissues to excess radiation. That is, illumination of lips and gums with high intensity actinic light can cause burns and thus is a limiting factor to the intensity of light that can be emitted safely from mouthpieces that use LEDs as the actinic light source. An example of a commercially available LED-illuminated mouthpiece is the GloBrilliant® Teeth Whitening Device (GloScience, New York, N.Y.), which emits light energy at less than 40 milliwatts per square centimeter when measured under simulated usage conditions. Examples of projector-type teeth whitening devices include the GoSmile® Smile Whitening Light (GoSmile Inc, Berkeley, Calif.) and the Luster® 1-Hour White® teeth whitening device (Dentovations, Boston, Mass.). Both of these devices also emit light energy at less than 40 milliwatts per square centimeter when measured under simulated usage conditions.

There is thus a need for improved methods and devices for whitening teeth using oxidizing agents and actinic energy of safe wavelengths and sufficient power density to enhance and speed whitening. In particular, there is a need for tooth whitening methods and devices capable of whitening teeth quickly, easily, and safely, and that limit the ability of the user to apply the actinic radiation to areas other than intended, eliminate the risk of harming tooth enamel, dentin, pulp or soft tissues in the oral cavity, can be adapted for consumer use, and apply an oxidizing agent to the teeth in the minimum amount necessary for effective bleaching of the tooth surface while limiting exposure of soft tissues to the oxidizing agent.

SUMMARY OF THE INVENTION

It is a general object of the invention to provide tooth whitening devices and methods that use actinic radiation in combination with exogenously applied oxidizing agents to whiten teeth quickly and safely. In that respect, it is another object of the invention to provide an actinic light emitting source with a light output that is optically connected to a reservoir containing a tooth whitening composition delivered directly to a stained tooth surface. In one form, the reservoir contacts the tooth surface and positions the light source a distance of less than about 15 mm therefrom, and preferably within 10 mm.

It is still another object of the present invention to deliver at least 100 milliwatts per square centimeter of actinic light energy to a stained tooth surface through a reservoir window and through a tooth whitening composition in the reservoir. To that end the reservoir has a portion that is substantially transparent to the wavelengths of the actinic radiation emitted by the light source, and the tooth whitening composition is formulated also to be substantially transparent to such wavelengths, such that the emitted light passes through both the reservoir and the whitening composition to reach the stained tooth surface without a significant reduction in light intensity. In a preferred form the tooth whitening composition includes an oxidizing compound capable of enhanced photobleaching of tooth stain chromogens in the presence of visible actinic light in a wavelength range between 400 and 700 nanometers (nm), without the use of excessive amounts of the oxidizing compound.

In one preferred form the present invention comprises a compact, ergonomic hand-held instrument that includes an actinic light emitting source such as a light emitting diode and a replaceable applicator cup as a reservoir for a tooth whitening composition held in place by the user against one of his or her teeth during a bleaching operation. The instrument may optionally include a source of secondary energy such as sonic, ultrasonic, electric, magnetic, electromechanical, mechanical or vibrational energy, or combinations thereof. In a preferred embodiment the secondary energy comprises mechanical vibration of the instrument while the applicator cup is in contact with the user's tooth.

In one broad aspect of the claimed subject matter, a container for a tooth whitening composition comprises a hollow, rigid cylindrical container body having a distal end and a proximal end with a mount for attaching the container body to a dental instrument that emits actinic radiation within a predetermined range of wavelengths, a window spaced from the proximal end of the container body in the path of the actinic radiation from the dental instrument, the window being substantially transparent to the actinic radiation, and a hollow, flexible cylindrical sleeve connected to the container body and extending to a distal end spaced from the proximal end of the container body, wherein the sleeve and the container body form a reservoir open at the distal end of the sleeve for holding a tooth whitening composition in contact with a tooth surface.

In another aspect of the claimed subject matter, one or more containers are provided as part of a kit for use by a non-professional to whiten teeth by applying a tooth whitening composition to a tooth surface while exposing the tooth surface to actinic radiation within a predetermined range of wavelengths. According to this aspect, a container includes a hollow, rigid cylindrical container body that is substantially circular in transverse cross section and has a distal end, a proximal end having a mount for removably attaching the container body to a dental instrument, and a window molded as a single piece with the container body and being substantially transparent to the actinic radiation, and a one-piece hollow, flexible cylindrical sleeve that is substantially circular in transverse cross section molded in place on the container body with at least a portion of the sleeve overlapping the outside surface of the body, wherein the sleeve and the container body form a reservoir open at a distal end of the sleeve for holding a tooth whitening composition substantially transparent to the actinic radiation. The kit also includes a dental instrument that includes an instrument body having a distal end with a mounting boss for accepting the container mount and a handle portion for the user to position the open distal end of the reservoir with a tooth whitening composition in the reservoir in contact with a tooth surface, and an actinic radiation source within the instrument body for emitting actinic radiation within a predetermined range of wavelengths through a tooth whitening composition in the reservoir and the window without substantially attenuating the intensity of the actinic radiation emitted by the radiation source.

In other aspects, the flexible sleeve is opaque to the actinic radiation and is molded in place over substantially the entire outside surface of the container body to prevent exposing soft mouth tissues to potentially harmful actinic radiation. In that regard, the instrument can further include a safety feature that terminates power to the source of actinic radiation in the instrument unless the cup is pressed into contact with a tooth surface of the user.

Another aspect of the invention resides in a dental instrument for use by a non-professional to whiten teeth by applying a tooth whitening composition to a tooth while exposing the tooth surface to actinic radiation within a predetermined range of wavelengths, in which the instrument comprises an instrument body having a distal end with a mounting boss for accepting a container with a reservoir for holding a tooth whitening composition, the instrument body further having a handle portion for the user to position an open end of the reservoir in contact with a tooth surface of the user. An actinic radiation source within the instrument body emits actinic radiation within a predetermined range of wavelengths through a window in the container and the tooth whitening composition in the reservoir without substantially attenuating the intensity of the actinic radiation emitted by the radiation source. In this aspect of the invention the instrument also comprises a safety cut-out for terminating power to the actinic radiation source unless a predetermined force is applied to the distal end of the device in a direction that holds the open end of the reservoir in contact with a tooth surface.

In a more specific form, such an instrument further comprises a neck portion pivotally attached to the handle portion, with the mounting boss at a distal end of the neck portion, wherein the safety cut-out includes a safety switch operated by pivoting movement of the neck portion relative to the handle portion and a spring biasing the neck portion into a position maintaining the switch in an open state wherein power is not supplied to the actinic radiation source, the switch being placed in a closed state when the neck portion is pivoted about the handle in the direction that holds the open end of the reservoir in contact with the tooth surface.

Certain method aspects of the invention involve whitening teeth by applying a tooth whitening composition to a tooth while exposing the tooth surface to actinic radiation within a predetermined range of wavelengths. This method comprises providing a dental instrument having a distal end with a mounting boss for accepting a container with a reservoir for holding a tooth whitening composition, a handle portion, and an actinic radiation source within the instrument body for emitting actinic radiation within a predetermined range of wavelengths of visible light through an window in the container and attaching the container to the mounting boss. The handle portion of the instrument is used to place an open end of the reservoir against a tooth to bring a tooth whitening composition in the reservoir into contact with a surface of the tooth, and the actinic radiation source is powered on to emit radiation through the window in the container and through the tooth whitening composition in the reservoir without substantially attenuating the intensity of the actinic radiation emitted by the radiation source and expose the tooth surface to the actinic radiation for a predetermined period of time. More specific forms of the method use visible light comprising wavelengths between about 400 nm and 700 nm, provide a distance from a light emitting surface of the actinic radiation source and the tooth surface is between about 10 mm and 15 mm, and subject the tooth surface to a light intensity of at least about 100 milliwatts per square centimeter.

It is yet another object of the present invention to provide tooth whitening methods that utilize actinic radiation in combination with other oral hygiene regimens that have been described by the present inventor, such as the cleaning and whitening methods disclosed in co-pending U.S. application Ser. No. 13/565,668 in the name of the assignee of the present invention, the disclosure of which is incorporated by reference as if set out in full herein. (See also Intl. Publ. No. WO2011/133793.) That application discloses a method of cleaning and whitening teeth in which an oxidizing composition is applied to the teeth, a protective coating or film is applied over the oxidizing composition, and the teeth are cleaned and scaled in proximity to the gum line, gingival margins, and crevicular spaces while the oxidizing composition and the protective coating or film are in place. An aspect of the present invention uses an instrument in accordance with the present invention to apply the oxidizing composition while subjecting the teeth to actinic radiation and, optionally, secondary energy. The instrument described herein can be used at any stage of the cleaning and whitening method disclosed in U.S. application Ser. No. 13/565,668 that involves applying an oxidizing composition.

Still another object of the invention is to implement an oral hygiene protocol using actinic radiation to reduce the numbers and types of oral pathogens in the mouth, the advantages of which have been described by the present inventor in co-pending U.S. application Ser. No. 13/658,517 in the name of the assignee of the present invention, the disclosure of which is incorporated by reference as if set out in full herein. One aspect of the present invention uses an instrument as described above during any stage of the cleaning and whitening method disclosed in U.S. application Ser. No. 13/565,668 to that object, although in a preferred aspect the instrument is used to apply actinic radiation in the initial stages of the methods described in that application. The instrument can also be used in a separate procedure to reduce the number of oral borne pathogens.

This Summary is provided to introduce a selection of concepts in a simplified form that are further described below in the Detailed Description. This Summary is not necessarily intended to identify key features or essential features of the claimed subject matter, nor is it intended to be used as an aid in determining the scope of the claimed subject matter.

BRIEF DESCRIPTION OF THE DRAWINGS

The objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

FIG. 3 is a cross section of the instrument in FIGS. 1 and 2 taken along the length of the instrument, and FIG. 3A is a detail view of the portion marked in FIG. 3, showing the safety switch open to prevent inadvertent activation of the instrument.

Figure 1:
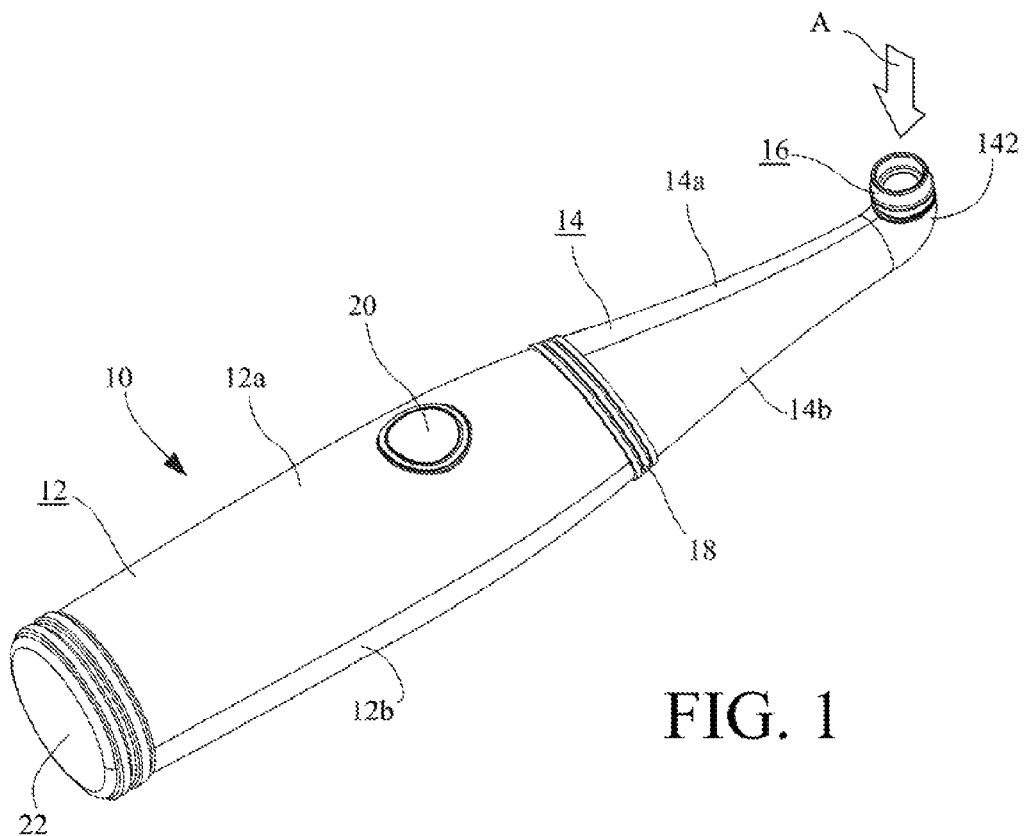
FIG. 1 is a perspective view of a hand-held tooth whitening instrument in accordance with an embodiment of the present invention.

Those skilled in the art will readily understand that the drawings in some instances may not be strictly to scale and that they may further be schematic in nature, but nevertheless will find them sufficient, when taken with the detailed descriptions of preferred embodiments that follow, to make and use the present invention.

DETAILED DESCRIPTION OF EXEMPLARY EMBODIMENTS

The detailed description that follows is intended to provide specific examples of particular embodiments illustrating various ways of implementing the claimed subject matter. It is written to take into account the level of knowledge of one of ordinary skill in the art to which the claimed subject matter pertains. Accordingly, certain details may be omitted as being unnecessary for enabling such a person to realize the embodiments described herein. It will also be understood that terms indicating direction or orientation, such as "lower," "upper," "top," "bottom," etc., may be used to facilitate the description of these exemplary embodiments. The use of such terms does not imply that the claimed subject matter is limited to a particular orientation of the structure being described.

It should also be understood that the description herein is set forth only to illustrate exemplary embodiments of the claimed subject matter, and in no way limits such subject matter to what may be referred to herein as preferred or possible ways of practicing the same. Moreover, the present disclosure is written for those skilled in the art to which the claimed subject matter is directed, and is not intended as a primer on the manufacture of tooth whitening compositions or their use, or on devices for using such compositions. Accordingly, certain basic concepts and standard features of devices or compositions well known to those practicing in the field are not set forth in detail. Likewise, exhaustive descriptions of principles involved in practicing the claimed subject matter, such as choosing appropriate construction materials or ingredients, operating conditions, manufacturing techniques, electrical circuitry, electronic components, and software/firmware that perform the functions described herein, and so forth, are omitted for the sake of brevity. Those skilled in the art will readily determine all of the information required to implement the claimed subject matter from the description herein, and attention is directed to appropriate texts and references known to those skilled in the art for details regarding any concepts and principles not covered in detail herein that may be required in the practice of the claimed subject matter. For example, basic information on the chemistry of tooth whitening and tooth whitening compositions may be found in reference works such as the *Kirk-Othmer Encyclopedia of Chemical Technology*. 4th Edition, Volumes 4 (1992), 13 (1995), and 18 (1996), John Wiley & Sons, NY; Goldstein and Garber, *Complete Dental Bleaching*, Quintessence Publishing Co. (1995); and the *Journal of the American Dental Association*, Vol. 128, Special Supplement (April 1997). The disclosures of these reference works are incorporated by reference to the extent they provide background information that might aid in understanding the discussion that follows.

Overall Description of Illustrated Embodiment

FIG. 1 is a perspective view of a hand-held tooth whitening instrument 10 in accordance with the presently described embodiment of the invention. For purposes of the present description the instrument 10 can be considered as having an instrument body with a proximal handle portion 12 that the user grips during use and a neck portion 14. As discussed in more detail below, the handle portion 12 is made in two halves 12*a* and 12*b*, and the neck portion 14 is also made in two halves 14*a* and 14*b*. An applicator cup 16 at the instrument's distal end provides a reservoir for a tooth whitening composition that a user holds in contact with a tooth using the handle portion 12. The applicator cup 16 represents an important aspect of the invention, and is described in detail further below with particular reference to FIGS. 5 to 7. The neck portion 14 is pivotally mounted to the handle portion 12 by a hinge assembly inside the instrument and thus not visible in FIG. 1. The hinge assembly permits the neck portion to pivot a slight amount in the manner discussed further below, as part of an important safety feature built into the instrument 10 and described in detail with particular reference to FIGS. 3, 3A, 4, and 4A. A flexible bellows 18 seals the handle portion 12 and the neck portion 14 as they pivot relative to each other during use of the instrument. The bellows seal protects the interior of the instrument from exposure to any moisture that is present while it is used to whiten a user's teeth. The manner of operation of this seal is also described in detail further below.

The instrument 10 also includes an ON/OFF button 20 located ergonomically on the handle portion 12 so that a user's thumb naturally falls on the button as the handle is gripped in position for proper use of the instrument. As described in more detail in connection with FIGS. 2 and 3, the instrument is normally in its non-actuated condition, and the user must first press the button 20 to close a main switch inside the instrument that is connected electrically between the instrument's power supply and operative parts of the instrument including an actinic light source and a secondary mechanical energy source, as described in more detail further below. The device remains in its ON condition until the button 20 is pressed again, which interrupts the connection between the power supply and the instrument's operative parts. The user places the applicator cup 16 carrying an appropriate tooth whitening composition (described further below) against a tooth while the device is ON. The safety feature of the instrument requires the applicator cup to be pressed against the tooth being whitened with a force sufficient to pivot the neck portion 14 relative to the handle portion 12. This pivoting is necessary to actuate an internal safety switch (not shown in FIG. 1) required for supply of electrical power to the actinic light source, thus making it difficult for a user accidentally to actuate the actinic light source and misdirect it, say into his or her eyes. The proximal end of the instrument terminates in a removable cover assembly 22 for an internal battery compartment. In the present embodiment disposable batteries supply electrical power for the instrument, but in other embodiments it could include a cord for attaching to a public power main, or the instrument can use a rechargeable battery with the proximal end configured with a socket for connection to a battery charger base.

Figure 2:
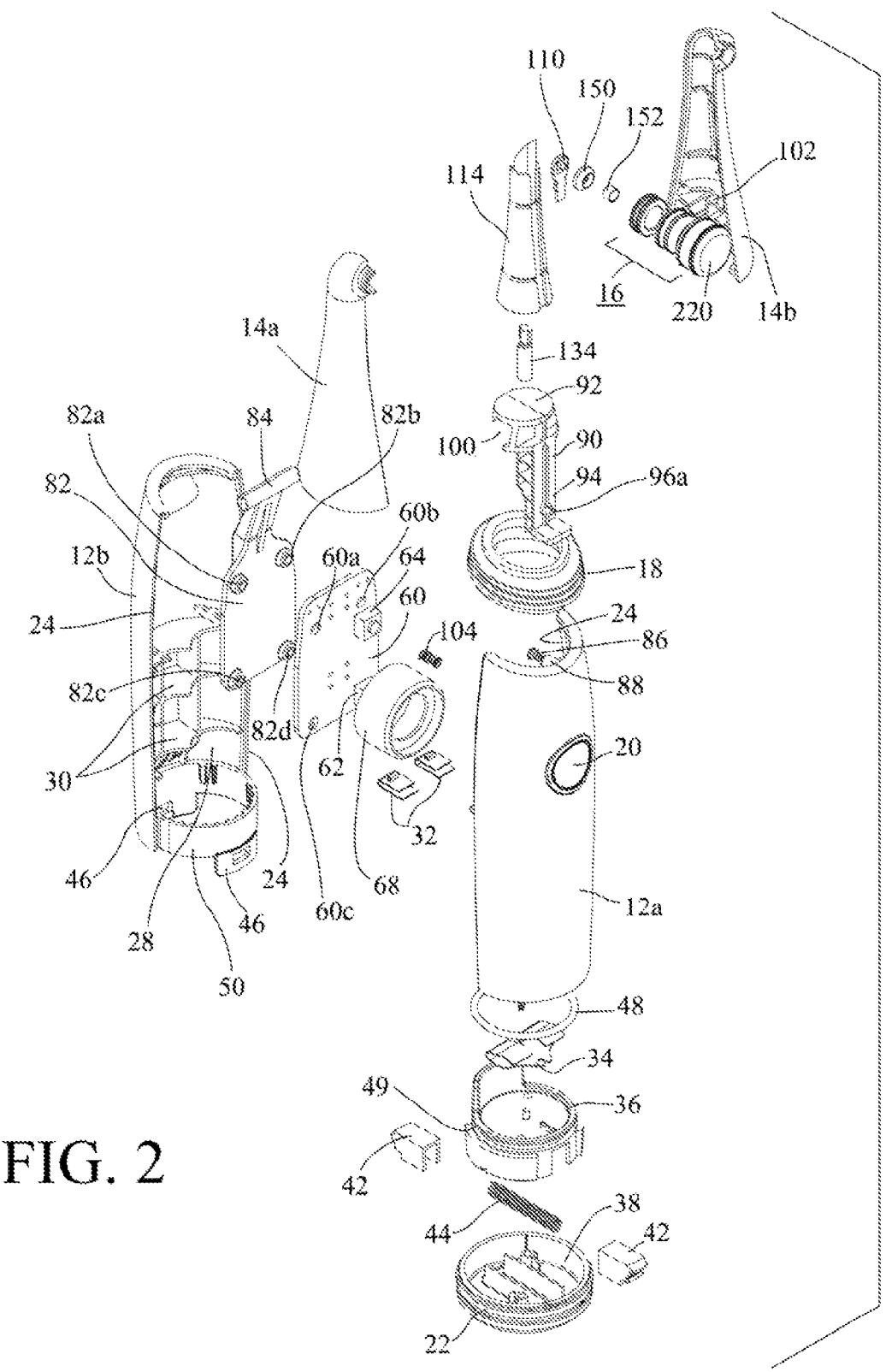
FIG. 2 is an exploded perspective view of the tooth whitening instrument in FIG. 1.

FIGS. 2 and 3 show the internal construction of the instrument 10. FIG. 2 is an exploded schematic view of the instrument showing its parts and FIG. 3 is a schematic cross section taken along the length of the instrument from its proximal end to its distal end through the applicator cup 16, the button 20, and the battery compartment cover 22. Beginning with the handle portion 12, its two halves 12*a* and 12*b* generally form a compartment that contains various parts of the instrument. The two halves each have stepped longitudinal edges 24 forming cooperating shoulders that nest when the edges are juxtaposed for assembly, thereby positively locating the halves 12*a* and 12*b* in their proper positions relative to each other in a fashion that is familiar to those skilled in the art. (The neck portion 14 has similar mating shoulders 14*s* best seen in detail in FIGS. 5 and 6.) The handle halves 12*a* and 12*b* are molded from a suitable plastic material that is durable and easily bonded, such as polycarbonate/acrylonitrile butadiene styrene (PC ABS), and they are bonded together in any suitable fashion, one being ultrasonic welding. This ensures that moisture and other contaminants, such as the tooth whitening compositions used with the instrument, cannot penetrate to the interior of the instrument and interfere with its proper operation.

The interior of the handle portion 12 includes a battery compartment 28, which in this embodiment is sized for two standard size AA batteries (not shown). Both handle halves 12*a* and 12*b* include internal ribs 30 that serve to define the battery compartment 28 and structurally stiffen the handle halves. Upper battery contacts 32 and a lower battery contact 34 provide an electrical connection to the batteries and the components of the instrument powered by them. These components are discussed in more detail below. The lower battery contact 34 mounts to an inner battery cover 36, which in turn is secured to an outer battery cover 38 to form the removable battery cover assembly 22. Two latch members 42, biased apart by a compression spring 44, are located in a space between the inner and outer battery covers 38. The latch members cooperate with respective catches 46 on the handle 12 to hold the battery cover assembly in place. With the battery cover assembly 22 latched into place on the handle portion 12, the internal ribs 30 locate the battery terminals relative to the battery contacts 32 and 34 and the cover assembly holds the battery terminals firmly against a slight spring force provided by the upper and lower battery contacts in a conventional manner. To replace the batteries, the user presses the latch members 42 together against the force of the spring 44 to release them from the catches 46 and permit removal of the battery cover assembly 22. An O-ring gasket 48 made of a suitable material such as EPDM rubber (ethylene propylene diene monomer) is held by a circumferential groove 49 molded in the inner battery cover 36. The O-ring 48 seals with a 360° flange 50 molded as part of the handle half 12*b* to prevent moisture from entering the battery compartment when the battery cover assembly 22 is hitched in place.

The instrument 10 further includes a main printed circuit board (PCB) 60 that carries the electronic components necessary for operation of the instrument. The PCB 60 carries circuit elements formed on the surface thereof in a conventional manner that need not be described here. The circuit is formed principally on the left side of the PCB as seen in FIGS. 3 and 3A, and on the back as seen in FIG. 2. The exact layout of the circuit on the PCB is not shown in the drawings, but it provides the connections and electronic components that cause the instrument to perform the operations described herein. Mounted to the side of the PCB 60 opposite that carrying the principal circuit connections and electronic components is a main button switch 62 and a safety button switch 64. These switches are shown in the drawings more or less schematically because they are readily available commercial components and a detailed description herein is not necessary to understand their operation. For purposes of the present discussion, reference is made to FIGS. 3 and 3A, which suggest the structure of the safety button switch 64 as having a switch body 64*a* that mounts the switch to the PCB 60 and an actuating plunger 64*b*. The actuating plunger 64*b* is biased to its outermost position by a compression spring (not shown) inside the body 64*a*, in which position the safety switch is closed to complete an electrical circuit. The main button switch 62 also includes a body 62*a* and an actuating plunger 62*b*, which is spring-biased to its outermost position in which the switch is open. Suitable switches for this purpose are made by Panasonic Corp. under part no. EVQPAC05 and assume their respective open and closed states when at least 100 gmf (grams-force) is exerted on their actuating plungers.

The ON/OFF button 20 is a membrane made of a flexible material, typically a thermoplastic elastomer (also known as thermoplastic rubber) with a Shore hardness of 50 on Durometer scale A. The membrane button 20 is molded in one piece with an outer boot 20a, which terminates in an outwardly directed sealing flange 20b, and a central column 20c. Pushing on the button in the direction of the arrow F causes the central column 20c to depress the switch button 62b and close the main switch 62. The button outer boot 20b is disposed with a slight clearance fit within a cylindrical boss 66 molded as part of the handle half 12a. A button holder tube 68, molded from a rigid plastic material such as PC ABS, fits snugly over the cylindrical boss 66 and has an internal flange 70, which is best seen in FIGS. 3 and 3A. When the handle portion has been assembled as described in detail further below in the discussion of the safety feature of the present embodiment, the internal flange 70 compresses the soft sealing flange 20b of the boot 20a against the end surface of the boss 66 to form a moisture-proof seal between the button 20 and the handle half 12a. The central column 20c of the button is aligned with the actuating plunger 62b of the main switch 62, and pressing on the button 20 with at least 100 gmf in the direction of the arrow F in FIG. 3 closes the main switch 62. The central column 20c can be molded with longitudinal stiffening ribs (not shown) on its exterior to inhibit compression of the column and thereby provide the user with greater positive tactile feedback when the button 20 has been depressed.

Pivoting Neck Portion Safety Feature

The neck portion 14 is pivotally mounted to the handle portion 12 by a pivot backbone 80 secured to the handle portion and a hinge leg secured to the neck portion and described in further detail just below. Together the pivot backbone and the hinge leg comprise a hinge assembly that permits the neck portion to pivot relative to the handle portion when a user of the instrument presses the cup 16 against a tooth to be whitened. Taking the pivot backbone first, it is molded from a rigid plastic material such as PC ABS with a backbone body 82 and a backbone pivot 84. See FIGS. 2, 3, 3A, 4, and 4A. The backbone body 82 is generally planar with a rectangular platform having four through-holes 82a, 82b, 82c, and 82d proximate to each corner of the rectangle. The main PCB 60 is also generally rectangular in platform and also has at its corners four through-holes, only three of which 60a, 60b, and 60c are shown in the drawings. Each of the holes 82a, 82b, 82c, and 82d is formed through a boss protruding from the surface of the backbone body 82 that faces the main PCB 60, as shown most clearly in FIG. 2. The cooperating holes in the PCB 60 are also shown in FIG. 2 (the fourth hole in the PCB is not shown in the drawings; it is hidden in FIG. 2 by the button holder tube 68). The bosses surrounding the holes 82a, 82b, 82c, and 82d end in reduced diameter portions that fit snugly into the respective through-holes in the PCB 60. A larger diameter portion of each boss forms a shoulder with the reduced diameter portion. This shoulder has a diameter larger than its corresponding hole in the PCB 60. Thus, the reduced diameter portion of each of the bosses around the holes 82a, 82b, 82c, and 82d fits into a corresponding hole in the PCB 60, while the larger diameter portion maintains a space between the backbone body 82 and the PCB 60. This both positively locates the pivot backbone 80 and the PCB 60 relative to each other, and provides a gap between the backbone body 82 and the electronic components formed on the facing surface of the PCB 60. This spacing can be seen in FIGS. 3, 3A, 4, and 4A.

Figure 4:
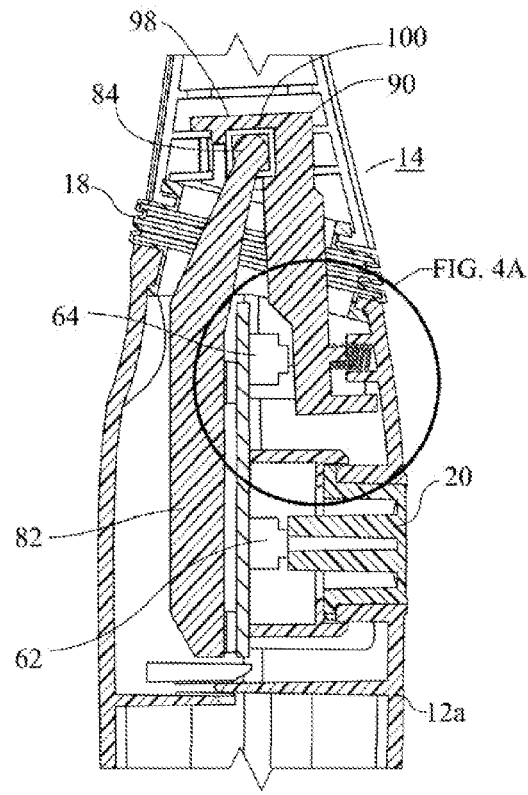
FIG. 4 is a portion of a cross section of the instrument as in FIG. 3.
Figure 4A:
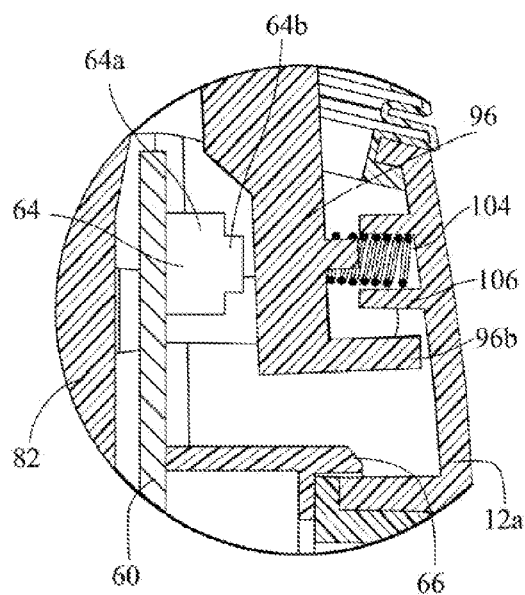
FIG. 4A is a detail view of the portion marked in FIG. 4, showing the instrument in its operative condition with the safety switch closed.

The pivot backbone 80 and the main PCB 60 are secured to the handle portion half 12a by screws 86 that pass through the holes 82a, 82b, 82c, and 82d and the corresponding holes in the PCB 60, and thread into pillars 88 molded into the interior of the handle half 12a. (Only one screw 86 and pillar 88 are visible in FIG. 2.) When the handle half 12a has been assembled, the outer boot 20b of the membrane button 20 is located in the cylindrical boss 66 on the handle half, and the button holder tube 68 is in place over the boss 66 with the outer sealing flange 20b of the membrane button 20 between the end of the boss 66 and the internal flange 70 of the button holder tube 68. The backbone body 82, with its bosses in the holes in the PCB 60, securely fastens to the handle half 12a by tightening the screws 86 into the pillars 88 with the button holder tube 66 compressed between the PCB 60 and the boss 66, as seen in FIGS. 3 and 4. This securely fastens the pivot backbone 80 to the handle 12, positively locates the PCB 60 for proper operation of the button switches 62 and 64, spaces the backbone body 82 from the circuit components on the PCB, and seals the membrane button to the handle. (For purposes of illustration, FIG. 2 shows screw 86 threaded into pillar 88 without the PCB 60 and the backbone body 82 in place.)

Figure 5:
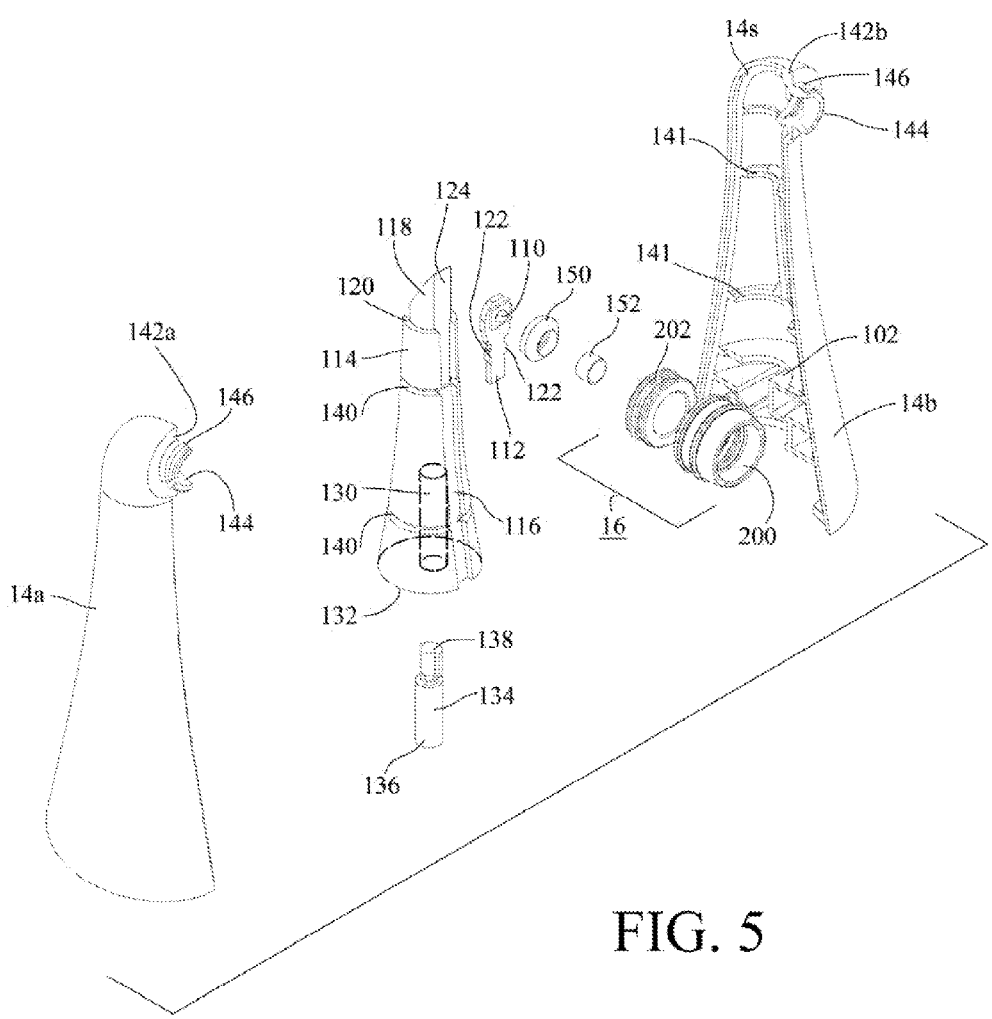
FIG. 5 is an exploded perspective view of the neck portion of the instrument shown in FIGS. 1 and 2, illustrating the relative locations of the actinic radiation source incorporated in the instrument, the applicator cup for holding a tooth whitening composition, and a vibratory motor providing a source of secondary energy in accordance with the present embodiment of the invention.

The hinge leg 90 is molded in one piece from a rigid plastic material such as PC ABS, and comprises a hinge leg pivot channel 92, a hinge leg body 94, and a hinge leg switch actuator 96. The hinge leg pivot channel 92 is molded at one end of the hinge leg body 94 with a flat top 98 for a purpose described further below and a female hinge channel 100 that accepts the backbone pivot 84 (see also FIGS. 3 and 4). The ends of the female hinge channel 100, which in cross section is a portion of a square, fit snugly over square bosses 102 molded into the neck portion halves 14a and 14b. (The square boss 102 in the neck portion half 14b is also shown in FIG. 5.) The backbone pivot 84 fits snugly into the female hinge channel 100 and the ends of the backbone pivot extend into and fit snugly within the bosses 102. The neck portion 14 is thus securely fastened to the handle portion 12 in a manner that permits the neck portion to pivot about the hinge formed by the backbone pivot 84 and the hinge channel 100.

This pivoting mounting of the neck portion 14 to the handle portion 12 provides in the present embodiment the safety feature that is one important aspect of the present invention. To that purpose, the hinge leg switch actuator 96, disposed at the end of the hinge leg body 94 opposite the pivot channel 92, includes a spring post 96a and a pivot stop 96b, best seen in FIGS. 3A and 4A. The spring post 96a fits into one end of a compression safety spring 104, the other end of which fits into a hollow boss 106 molded into the interior of the handle portion half 12a. The safety spring 104 biases the hinge leg 90 clockwise about the hinge channel 100 (as seen in FIGS. 3 and 4). This spring force presses the hinge leg switch actuator 96 into the safety switch actuating plunger 64b with a force sufficient to maintain the plunger down and the safety switch 64 open in the absence of any countervailing force. This state is shown in FIGS. 3 and 3A. However, if a user presses the applicator cup 16 against a tooth with a predetermined force A, the force pivots the neck portion 14 about the hinge formed by the backbone pivot 84 and the hinge channel 100 in the direction of arrow P in FIG. 3. The hinge leg now assumes the state shown in FIGS. 4 and 4A, in which the safety switch actuating plunger 64b has been moved outwardly by the switch 64's internal compression spring to close the switch. Rotation of the hinge leg 90 in the actuating direction P is terminated by contact of the hinge leg stop 96b with the inside of the handle portion half 12a, as seen in detail in FIG. 4A, which limits the rotation of the neck portion to an arc of about 1° to 5°. Depressing the safety switch plunger 64b by the hinge leg, as discussed above, prevents at least the actinic light source from being energized. This aspect of the instrument operation is described in further detail below.

The bellows seal 18 is molded from a flexible material, and for convenience and economy of manufacture can be the same thermoplastic elastomer as the membrane button. The bellows seal includes circumferential channels that fit snugly around circumferential rims molded around the top opening of the handle 12 and the bottom opening of the neck portion where they join together in accordance with FIG. 2's exploded view. These parts are all sized and oriented in a manner that will be readily understood by one skilled in the art so that the circumferential rims of the assembled handle 12 and neck portion 14 shown in FIGS. 3 and 4 compress the circumferential channels in the bellows to form a moisture-proof seal therebetween. The bellows thus permits the limited rotation of the neck portion about the hinge formed by the backbone pivot 84 and the hinge channel 100, discussed above, while preventing moisture and other foreign substances from entering the interior of the instrument where the neck portion 14 pivotally connects to the handle portion 12.

Applicator Cup and Energy Enhancement

Figure 6:
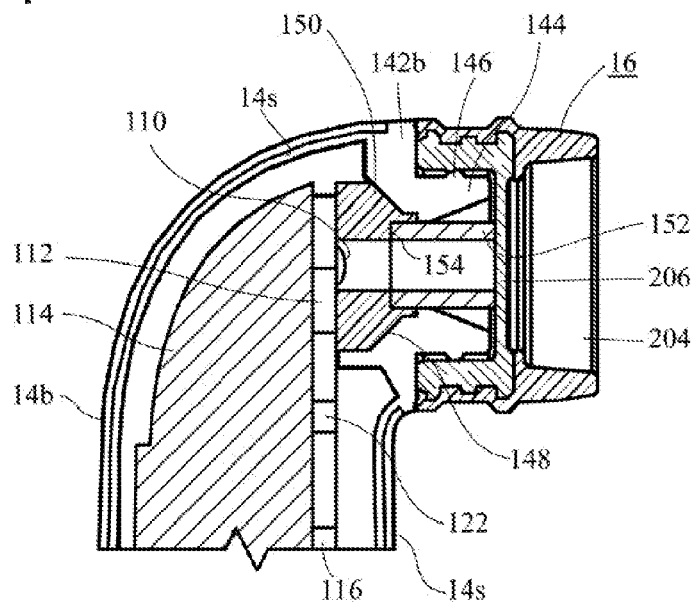
FIG. 6 is a detailed cross-sectional view taken from the marked portion of FIG. 3 further illustrating details of the applicator cup construction and the relative locations of the actinic radiation source and the applicator cup.

The novel applicator cup 16 on the instrument holds a whitening composition in contact with a user's tooth, as described in detail further below, while the instrument applies actinic light and secondary energy, in this embodiment mechanical energy, to the tooth being whitened. In the present embodiment the neck portion 14 holds an actinic light source and a source of mechanical energy in a fashion that is best seen in FIGS. 2, 5, and 6. The actinic light source comprises a light emitting diode (LED) 110 that emits actinic radiation in wavelengths and at powers suitable for the purpose, as discussed in detail further below. The LED 110 is carried by an LED printed circuit board 112 that enables electrical connections to be made to the LED. This is a conventional construction and need not be described in detail for those skilled in the art to be able to provide a suitable LED actinic energy source in accordance with the present embodiment of the invention. The neck portion 14 holds a solid metal heat sink 114 cast from a material that is a good heat conductor, such as a copper, brass, or an aluminum alloy. (The heat sink 114 is omitted from FIGS. 3 and 4 for clarity.) The heat sink 114 includes a main longitudinal groove 116 running the length of the heat sink, and this groove provides space for running wires (not shown) to the LED PCB 112 from the appropriate circuit components on the main circuit board 60 in order to provide electrical power to the LED. At the top the heat sink has a reduced diameter portion 118 that provides a circumferential shoulder 120 interrupted at the location of the groove 116. The edges of the shoulder at the groove 116 bear against tabs 122 on the sides of the LED PCB 112 to aid in properly locating the LED. The back surface of the LED PCB is bonded to the heat sink 114 in the groove 116 and on the flat surface 124 on the reduced diameter portion 118. The surface of the groove 116 and the flat surface 124 are flush to enable the LED PCB 112 to be bonded over substantially its entire back surface to the heat sink 114, thus ensuring optimum heat transfer from the LED to the heat sink 114.

The heat sink 114 is cast with a blind hole 130 extending longitudinally into the heat sink interior from its flat bottom surface 132. The blind hole 130 accepts a vibratory motor 134 with a cylindrical motor body 136 that fits snugly within the blind hole 130 and a motor shaft that carries an eccentric mass 138. The motor body 136 is disposed wholly within the hole 130 in the heat sink and is bonded securely to the inside surface of the hole to embed the motor in the heat sink so that the vibration generated by rotation of the motor's eccentric mass is transferred directly to the heat sink 114 with minimal energy loss. The vibratory motor 134 is most conveniently a commercially available product, and a suitable motor for the purpose is a 4 mm diameter motor available from Precision Microdrives Ltd. of London, UK, under model no. 304-002. Wires (not shown) extend from the bottom of the motor, into the space between the top 98 of the hinge leg 90 and the bottom 132 of the heat sink 114, and are connected to the appropriate circuit components on the main circuit board 60 in order to provide electrical power to the motor 134. In a preferred embodiment the motor's eccentric mass rotates at an angular velocity between 8,000 and 16,000 rpm (that is, at a frequency between about 130 to 270 Hz).

The vibratory motor 134 is dynamically coupled to the neck portion 14 by coupling grooves 140 that are cast into the surface of the heat sink 114 and that fit onto orientation ridges 141 molded into the neck portion halves 14a and 14b (only the ridges in the half 14b are visible in the drawings). This arrangement maximizes the amount of the mechanical secondary energy imparted by the motor embedded in the heat sink that is applied to the user's tooth during a whitening operation. The ridges also serve to positively locate the LED, which is bonded to the heat sink 114, in the proper position for projecting light through the applicator cup 16, as seen in detail in FIG. 6, which is a cross sectional view showing details of the construction of the distal end of the instrument with the applicator cup 16 in place. The two neck portion halves 14a and 14b are molded with respective instrument head halves 142a and 142b having facing surfaces that are bonded together to form an instrument head 142 for mounting the applicator cup 16. As seen in FIG. 6, the orienting shoulders 14s do not extend into the instrument head facing surfaces, which are thus bonded in surface-to-surface contact to create a stronger bond that will better withstand repeated removals and attachments of applicator cups 16 over the life of the instrument. In addition, since the applicator cup is pressed against a tooth during use of the instrument, more surface area is bonded together in the head region where the cup is mounted to provide a more robust construction.

The instrument head 142 includes a circular cup-mounting boss 144 with a circumferential ridge 146 that cooperates with tabs on the applicator cup 16, as discussed in more detail below. The inner surface of the boss includes an inward facing countersunk surface 148 that mates with a beveled LED seal 150 molded from a flexible material, which for convenience and economy of manufacture can be the same thermoplastic elastomer as the membrane button 20 and the bellows seal 18. The countersunk surface 148 on the boss and the beveled face of the seal 150 both subtend an angle of about 45° to form a close surface-to-surface seal therebetween. The parts of the neck portion and the heat sink that backs up the seal 150 are sized so that the beveled face of the seal 150 is wedged against the countersunk surface 148 to seal them together against the entrance of moisture and other contaminates. That is, the heat sink 114 is held in place in the neck portion by the locating ridges 142 so that the face of the LED PCB 112 is pressed firmly against the inside surface of the LED seal 150, which in turn is pressed firmly against the countersunk surface 148 to prevent foreign substances from entering the interior of the instrument through the open end of the boss.

Completing the instrument head is a reflector tube 152 that extends from within the LED seal 150 toward the back side of the applicator cup 16. The inside end of the reflector tube bears against an internal shoulder 154 in the seal 150 to properly position the reflector tube so that there is a small clearance between the tube's external end and the back side of the applicator cup 16 when the latter is in place on the cup-mounting boss 144. The reflector tube 152 is conveniently made of metal and has a mirror-like finish on its interior that maximizes the amount of actinic energy available at the tooth surface even though the LED is held wholly within the instrument and is thus necessarily spaced from a user's tooth. The reflector tube can also be molded from plastic and have a metallic reflecting layer deposited on its inner surface. In another alternate construction, the reflector tube is omitted and the mounting boss 144 is white or has a metallic reflecting layer vacuum formed on its inside surface. In the present embodiment the reflector tube 152 is bonded to or friction-fitted within the LED seal 150 so that the reflector tube 152, which in one embodiment is only 4 mm in diameter, does not become dislodged from the instrument and lost.

Figure 7:
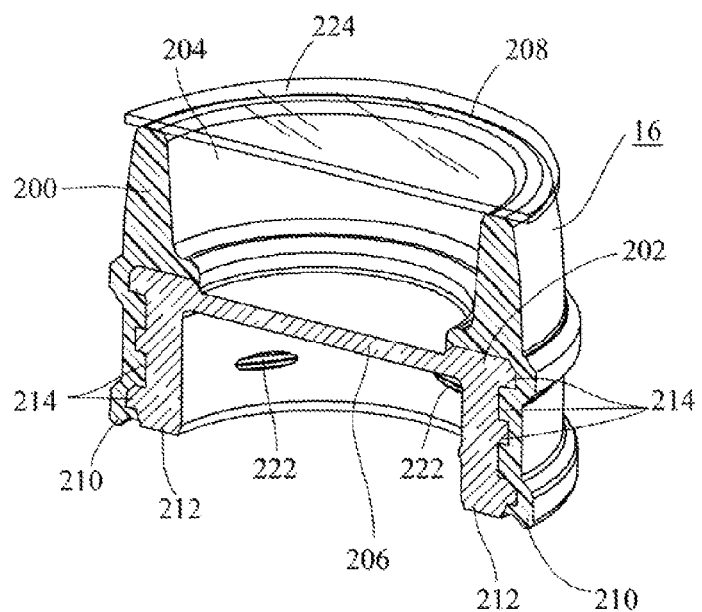
FIG. 7 is a perspective cross-sectional view of the applicator cup of the present embodiment taken along a plane including the centerline of the cup.

Turning now to a particularly important aspect of the present invention, the novel applicator cup 16 will be described with primary reference to FIG. 7. To understand some of the criteria that are taken into account in making the cup, it will be helpful to understand its purpose and operation as a user applies a tooth whitening composition with the instrument 10 in accordance with the invention. One of the objects of the invention is to provide a tooth whitening procedure that enhances the whitening effect of compositions applied to the teeth using oxidizing agents and actinic energy at sufficient power levels and safe wavelengths to enhance and speed whitening. It is particularly designed to be capable of use by a consumer (that is, outside of a dental office without the participation of a professional) to whiten teeth quickly, easily, and safely, while also (i) limiting the ability of the consumer to apply the actinic radiation to areas other than intended, (ii) eliminating the risk of harming tooth enamel, dentin, pulp or soft tissues in the oral cavity, and (iii) applying an oxidizing agent to the teeth in the minimum amount necessary for effective bleaching of the tooth surface while limiting exposure of soft tissues to the oxidizing agent.

The cup 16 comprises one of the vehicles for achieving these objects by virtue of its outer flexible opaque sleeve 200 molded in place over an inner rigid transparent body 202. The sleeve 200 and the body 202 are hollow circular cylinders (that is, they have a circular cross section transverse to the cylinder axis), and together they form a reservoir 204 for a tooth whitening composition. The bottom of the reservoir is formed by a clear plastic window 206 that is part of the body 202, through which window actinic light from the LED 110 passes for impingement on the tooth surface. Thus, the reservoir 204 is bounded by the side wall of the sleeve and the window 206. In use, a tooth whitening composition, typically an oxidizing compound, is held in the reservoir. In that respect, making the outer sleeve from a flexible material will permit it to conform to the contour of the tooth being treated when it is pressed against the buccal (front) surface of the tooth. This will aid in preventing the tooth whitening composition from flowing out of the reservoir while the tooth is being treated and maximize the time that the composition is held in contact with the tooth. The various parts of the instrument head and the applicator cup are dimensioned so the distance from the light source (that is, the surface of the LED 110 in the present embodiment) is no more than about 15 mm from the distal end of the sleeve that contacts the tooth surface. It is believed that a distance greater than 15 mm will attenuate the amount of light energy reaching the tooth surface sufficiently to mitigate the enhancing effect of the actinic radiation in the bleaching process. This aspect of the invention is discussed further below in connection with tooth whitening methods and compositions in accordance with the invention.

In combination with the safety feature discussed above, making the sleeve 200 opaque to the actinic light emitted by the LED, and molding it so that it overlaps the outside of the body 202, effectively prevents areas of the user from being inadvertently exposed to the actinic light during normal use of the instrument. That is, as described above, the LED will not be supplied with electrical power unless the distal end rim 208 of the sleeve 200 is pressed against a user's tooth with sufficient force to pivot the neck portion 14 about the hinge formed by the pivot backbone 80 and the hinge leg 90. The sleeve material and configuration are chosen so that the force necessary to energize the LED conforms the sleeve tightly to the tooth surface to form a seal therewith. Thus, with the sleeve being opaque to the actinic light, the actinic radiation is directed solely to the user's tooth. In that respect, the proximal end 210 of the side wall of the sleeve 200 extends generally all the way to the proximal end 212 of the annular side wall of the body 202 to prevent soft mouth tissues of the user from being exposed to any actinic light that might leak from between the end of the reflecting tube 152 and the inside of the window 206 (see, for example, FIG. 6).

The sleeve 200 may be made from any material that meets the above operational criteria, but for convenience and ease of manufacture it can be the same thermoplastic elastomer as the membrane button 20, the bellows seal 18, and the LED seal 150. The body 202 is made of a rigid plastic material over which the sleeve 200 can be molded in place. A suitable material is a PC ABS resin from which many of the parts discussed above are made, although the resin will necessarily be formulated so that the body is transparent to the actinic light emitted by the LED 110. (Suitable constructional materials include polycarbonate, polystyrene and clarified polypropylene, which are also sufficiently rigid and transparent) For purposes of the present discussion, a "transparent" window is one that transmits at least 25%, more preferably at least 50%, and most preferably at least 75%, of actinic light comprising wavelengths between 350 nm and 700 nm. In a preferred embodiment the sleeve 200 and body 202 form what essentially functions as a single piece, enhanced by using for the sleeve a thermoplastic elastomer that inherently adheres to the material used for the body, with optional interlocking ridges 214 where the sleeve overlies the body side wall. Other functions of the flexible sleeve include providing a more positive grip for an optional cap cover 220 (shown only in FIG. 2), and providing a tactile surface that makes it easier for the user to handle the relatively small size of the applicator cup 16. The cap cover, which can also be made of a PC ABS or polypropylene resin, preferably forms a friction fit with the sleeve 200 and is thus easily removed when the instrument is to be used.

To summarize some of the important parameters of an exemplary preferred embodiment of the instrument 10, the LED 110 is a Luxeon® Rebel LXM L-PR01-0500 royal blue light emitting diode (Philips Lumileds Lighting Co., San Jose, Calif.), with a nominal output rating of 500 milliwatts at 350 mA, that emits blue light comprising wavelengths between 400 nm and 500 nm, with a peak wavelength of approximately 455 nm. The light emitting surface of the LED is approximately 7 mm from the surface of the tooth being treated and the light transmission properties of the cup body with the window 206 and of the tooth whitening composition in the reservoir 204 are such that approximately 200 milliwatts per square centimeter of actinic light are delivered to the tooth surface. The reservoir window 206 has a diameter of 8 mm, and the reservoir distal end 208 is spaced 2 mm from the window along the axis of the cylindrical sleeve 200. The flexible sleeve wall is about 1 mm thick and the reservoir has an internal volume of approximately 100 cubic mm (0.1 cubic centimeters).

The applicator cup 16 is removably mounted to the cup-mounting boss 144 and replaceable with another applicator cup. As alluded to above, the wall of the body 202 in the depicted embodiment includes internal mounting tabs 222 that are shown in FIG. 7 spaced at regular locations around the circumference of the wall (say at 90° intervals). When the open end of the cup body is pressed into place over the cap-mounting boss 144, the tabs 222 snap over the circumferential ridge 146 (see FIG. 6) to hold the cup onto the boss 144. The proximal end 210 of the sleeve 210 extends slightly beyond the proximal end of the body wall 212 so that when the cup is in place as shown in FIG. 6, the proximal ends of the sleeve wall are compressed slightly against the outward face of the cup-mounting boss 144 to provide a slight force urging the tabs 222 against the ridge 146, which aids in holding the cup against undesired movement and also seals it to the mounting boss while the instrument is in use. Other arrangements for removably attaching the cup 16 to the mounting boss 144 will occur to those skilled in the art, such as a bayonet mount, a magnetic mount, or even a threaded connection. The present invention is clearly not limited to any particular cup mounting arrangement.

Making it easy to remove and replace the applicator cup 16, while preserving all of the other advantages of the invention already discussed, is an important further aspect of the invention. As already noted, the invention permits a user to treat one tooth at a time in a safe, convenient, and effective manner. However, since the volume of the reservoir for the tooth whitening composition is necessarily limited, it will require replacement during a procedure in which more than a few teeth are treated at a time. Conveniently, the cups can be sold prefilled with tooth whitening composition and covered with a removable plastic film 224 adhered to the distal rim of the sleeve. The user can then remove and discard cups as they empty of tooth whitening composition during a treatment procedure, snap a fresh applicator cup in place, remove the plastic film, and continue the procedure. Alternately, a separate container, such as a tube or syringe filled with a tooth whitening composition, may be used to manually replenish the cup with tooth whitening composition as needed during a tooth whitening procedure.

Operation of Instrument and Methods of Using Same

Typically, the instrument 10 will be provided to a user in kit form with one or more applicator cups 16 prefilled with a suitable whitening composition of a formulation having the properties described further below. A user can obtain additional separate prefilled applicator cups that will normally be sealed with a removable plastic film adhered to the rim of the sleeve 200. Alternatively, a user can obtain a desired whitening composition sold separately in a suitable paste, gel, or liquid form with which the user can fill an empty new or used applicator cup reservoir 204 and then cover the open distal end of the sleeve with the cap cover 220 to prevent the composition from inadvertently leaking until the moment the instrument is to be used. In any case when the user is ready to commence a tooth whitening procedure, he or she presses an applicator cup 16 onto the instrument mounting boss 144 until he or she feels the tabs 222 on the cup body snap into place over the circumferential ridge 146 on the boss. Just prior to use, the user removes the protective film from the distal end of the sleeve 200 of a prefilled cup, and/or the cap cover 220 if one has been placed over the sleeve 200. (It will be apparent that an empty reservoir of a cup can be also refilled while the cup is mounted on the instrument.)

The operational parts of a preferred embodiment of the instrument are, as already described, limited to turning the instrument ON and OFF using a single ON/OFF button 20.

The instrument will most preferably be under the control of a microprocessor (not shown) embedded in firmware carried by the main printed circuit board 60. Only the functions and operations of the instrument are described herein, it being clearly within the ability of one skilled in the art to formulate the necessary software code to implement the described operations and functions, or desired variations thereof, in accordance with the description that follows. In that regard, depressing the button 20 when the instrument is in power-OFF mode closes the main button switch 62, and sends a signal to the microprocessor on the main PCB that places the instrument in the power-ON mode until the button 20 is again depressed to close the main button switch 60. In the power-ON mode the vibratory motor 134 is energized, which provides to the user a tactile indication that the instrument is ready for use. The instrument may further include a visible indicator, such as a small auxiliary LED at a conspicuous location on the handle portion 12, that is lit whenever the device is in the power-ON mode. However, the microprocessor does not at this time power the main LED 110 for providing actinic radiation to a tooth surface.

When the applicator cup is pressed against a surface of a user's tooth, the neck portion 14 pivots slightly about the hinge formed by the backbone pivot 84 and the hinge channel 100. The hinge leg switch actuator 96 is moved against the force of the safety spring 104 to depress the safety switch actuating plunger 64b (see FIGS. 3A and 4A). The microprocessor receives a signal that the safety switch is closed and activates the LED 110. At this time the main LED 110 is actuated in addition to the vibratory motor 134, and the user moves the open end of the applicator cup sleeve over the surface of a tooth. The vibrations imparted by the motor 134 assist exposure of the tooth to fresh tooth whitening composition within the reservoir as the whitening procedure progresses, while the actinic light from the LED is directed at the tooth. The vibrations also facilitate movement of the applicator cup over the tooth surface by reducing the friction between the tooth enamel surface and the distal rim 208 of the thermoplastic elastomer cup sleeve 200. If the applicator cup is at any time raised from the tooth surface, the safety switch sends a signal to the microprocessor, which interrupts power to the main LED. As noted above, the motor 134, and the auxiliary LED if present, continue to receive power from the batteries to indicate to the user that the instrument is still in the power-ON mode. Pressing the main power button while the instrument is in its power-ON mode interrupts power to all of the device components, including the motor 134 and the auxiliary LED.

In one embodiment the instrument includes a buzzer (not shown) that provides an audible beep or other recognizable sound. The buzzer can take any suitable form, such as a piezoelectric device, under the control of a timer included in the microprocessor. When the microprocessor receives a signal from the safety switch 64 indicating that it is closed, the microprocessor begins counting down a predetermined time, preferably about 10 seconds. After the timer times out, the microprocessor causes power to be supplied to the buzzer indicating that the tooth surface has been treated with whitening composition and actinic light for a sufficient time. This signals the user to lift the cup from that tooth surface, which turns off the main LED, and move the cup to the surface of the next tooth to be treated. (The motor 134 remains activated.) Upon pressing the cup against the next tooth surface, the timer begins timing again. A maximum of 8 to 10 teeth can be effectively treated with a reservoir holding 100 cubic mm of a whitening composition meeting the criteria discussed below, although one skilled in the art will understand that greater tooth whitening efficacy can be achieved by replenishing the tooth whitening composition more frequently (either by removing the used applicator cup and attaching a new one to the device or refilling the mounted cup).

Summary and Examples of Possible Modifications and Additional Applications

Although the instrument 10 has been described in one particular form, with various modifications to the instrument itself or the method of using it already pointed out in the course of the above description, additional modifications are possible. For example, the microprocessor controlling the instrument could include software for detecting a low battery power condition, and in response send a signal to cause flashing of the auxiliary LED discussed above. In another modification, the safety switching mechanism described above involving a pivoting neck portion could be replaced by a capacitive switch for detecting a conductivity change when the applicator cup is in contact with an electrically conductive biologic surface such as tooth enamel, and permitting actuation of the LED when the conductivity change is detected. Yet another example of an alternate safety mechanism is a proximity switch that can detect when the applicator cup is a specified distance from a tooth surface. As disclosed, an instrument according to the invention may optionally apply one or more forms of secondary energy to a tooth being treated. In the embodiment described above the secondary energy is mechanical vibration, but other forms of secondary energy could include sonic, ultrasonic, electric, thermal, magnetic, electromechanical energy, and combinations thereof. These secondary energy sources can contribute to the speed and efficacy of the tooth whitening process by accelerating the oxidation of tooth stains, enhancing the penetration of tooth whitening compositions into the tooth enamel and dentin, or otherwise improving the tooth whitening outcome beyond that which is possible with just oxidation chemistry and actinic energy alone.

Other possible modifications include molding the window 206 as a lens to focus the actinic light onto the tooth surface being treated. In addition, although the applicator cup 16 is disclosed as having a two-piece molded construction, the claimed subject matter is not so limited. Simply as one example of an alternate construction, the cup could be made with a separate window molded or adhered within a flexible sleeve with a rigid mount at its proximal end.

To summarize certain method aspects of the invention, stained teeth may be treated individually, for instance, by directing the light emitted from the instrument 10 onto a single stained tooth surface through a transparent or partially transparent reservoir containing an oxidizing composition. In this manner, several stained teeth may be exposed in sequence to the actinic light and the oxidizing composition in the applicator cup 16, with the user moving the device from one tooth to the next during the procedure so that the applicator cup is in contact with each tooth in sequence for a specified period of time, typically between five and 60 seconds, and preferably between 10 and 30 seconds per tooth. Although the process may seem labor intensive and time consuming, it provides the option of whitening individual teeth, or even specific locations on a single tooth requiring stain removal, and provides a degree of precision in the application of an oxidizing composition along with actinic radiation that heretofore has been unavailable in the prior art, as discussed at the outset. In particular, an instrument in accordance with one aspect of the invention comprises a reservoir that not only provides a delivery vessel for the oxidizing composition, but also serves to (i) limit the migration of oxidizing composition onto the soft tissue surfaces in the mouth, and (ii) constrain the actinic light to just the area on the tooth in contact with the oxidizing compound in the reservoir. A prior approach like the Union Broach® Illuminator System described above provides direct, full spectrum, uneven illumination to all of the teeth found in the front of the average adult's mouth using a light source outside the patient's mouth. Since light intensity decreases in proportion to the inverse square of the distance from the illuminated surface, methods of whitening teeth described herein direct light of selected wavelengths at a single tooth, preferably with the light output located at a more or less constant distance of less than 15 mm, and most preferably less than 10 mm, from the tooth surface.

An adaptation of the method aspects of the invention could include using the instrument 10 or a variation thereof in the combination tooth dental prophylaxis and whitening procedures disclosed in U.S. application Ser. No. 13/565,668. Either integrated into one of the combination cleaning/whitening methods described in that application during an initial tooth conditioning step (such as chemo-mechanically removing acquired pellicle), or as a stand-alone adjunct to a simple dental prophylaxis, the instrument and methods described herein can be used to whiten teeth prior to, during, or after prophylaxis, which generally involves the removal of sub- and supra-gingival plaque and tartar by a dental hygienist. As an additional benefit to the patient, the exposure of gingival soft tissue in the oral cavity to actinic light during the use of the device may reduce the numbers and types of periodontal pathogens. A device in accordance with the above description, that is, an instrument with an applicator cup and an LED light source emitting blue light between 400 nm and 500 nm, with a peak wavelength of approximately 455 nm and a light intensity of 500 mW/cm$^2$, was shown to be capable of reducing the viability of periodontal pathogens in vitro with very short exposure times, as demonstrated by the tests described below in Example 5. Co-pending U.S. application Ser. No. 13/658,517 discloses the use of light sources other than an LED, with a range of wavelengths and intensities that can be used for this purpose.

The following is one example of a manner in which an instrument according to the present invention can be used in the simultaneous cleaning and whitening method described in U.S. application Ser. No. 13/565,668:

1. Using cheek and lip retraction implements into the oral cavity of the subject. This can be a cheek retractors and/or cotton rolls placed in such a way as to prevent the soft tissue of the inside of the lips and cheeks from coming into contact with the tooth surfaces.
2. Conditioning of the teeth surfaces to be whitened with a conditioning agent or conditioning composition, using chemical, mechanical, or chemo-mechanical means.
3. Contacting the conditioned tooth surfaces with one or more oxidizing agents placed in the applicator cup 16 of the instrument 10 described herein.
4. Contacting the tooth surfaces with a water-resistant coating or film-forming composition to protect the oxidizing agent from direct contact with external moisture during the tooth cleaning process.
5. Cleaning and scaling of subject's teeth in proximity to the gum line, gingival margins and crevicular spaces while the compositions of steps (3) and (4) above are in contact with the tooth surfaces.
6. Polishing the teeth with prophylaxis or polishing paste following completion of step (5).
7. Optionally repeating steps (3) and (4).
8. Cleaning and rinsing all residual materials from tooth and gum surfaces that were applied or produced during the performance of steps (1) through (7).

As disclosed in U.S. application Ser. No. 13/565,668, the compositions and/or agents of steps (2) to (4) may be combined into a single composition that is placed in the applicator cup 16. In addition, the patient may be supplied with a home use version of the instrument 10 with a supply of applicator cups prefilled with an oxidizing compound, as described above. The instrument 10 may be used as part of an oral hygiene protocol using actinic radiation to reduce the numbers and types of oral pathogens in the mouth, the advantages of which have been described by the present inventor in co-pending U.S. application Ser. No. 13/658,517. This can be done as part of a combined cleaning/whitening procedure before during, or after any of the steps outlined above, although more advantageously as part of step (2) or in a combination of steps (2) to (4) using a single composition as a conditioning agent/composition, oxidizing agent, and water-resistant coating or film-forming composition. It can also be performed as a separate stand-alone procedure. Further, the instrument can be used alone, or before or during steps (1) to (3) as part of a combined cleaning/whitening procedure, to reduce the number of and types of oral pathogens.

For purposes of the description herein, "light output" shall mean the location or surface on a device or object where light is emitted. For example, the light source of a light emitting diode (LED) in the absence of any auxiliary light transfer means (such as a lens or fiber optic light guide) would be the surface of the LED itself (which is typically some form of transparent polymer used to protect the LED semiconductor chip from moisture and air contamination). Alternatively, the light output of an LED that is optically connected to a focusing lens would be the emitting surface of the focusing lens. Another example would be a xenon flash lamp optically connected to a fiber optic light guide, where the light output would be considered the emitting surface of the end of the fiber optic light guide. The terms "optical output" and "light output" are used interchangeably, and an optical output or light output may have one or more light sources ("light source" meaning a component or components of a light emitting device that transforms non-light energy into light energy).

More specifically, light sources which emit actinic radiation in the wavelength range from about 350 nm to about 700 nm, and deliver about 100 to 2,000 milliwatts per square centimeter to a tooth surface, are especially preferred in methods according to the invention, in that tooth chromogen molecules responsible for tooth staining absorb primarily in this region of the spectrum. Light sources which emit actinic radiation in the wavelength ranges from about 350 nm to about 500 nm are most preferred. Suitable light sources which emit actinic radiation in the preferred range of wavelengths include an LED, as used in the instrument 10 discussed above, as well as linear flash lamps, tungsten halogen, metal halide, Xenon short arc, Mercury short arc, Mercury Xenon short arc, Argon plasma arc and Argon short arc lamps, and diode lasers, among others. LEDs are a preferred light source due to their small size, efficiency and low cost, as well as their ability to be incorporated into a hand-held instrument for use by a consumer. However, it will be appreciated that it would also be within the scope of the present invention to adapt an applicator cup such as that described herein for use with a dental curing light, which typically houses a high-powered LED that emits actinic light in the wavelength ranges from about 400 nm to 500 nm and is conventionally used to initiate photo-polymerization reactions in light-cured dental adhesives and composite restorative materials. Other types of light sources may be operatively connected by any suitable mechanism, such as an optical fiber waveguide, to the instrument for delivery of actinic energy to a tooth surface. In fact, any light source that can be adapted to accept and emit light through an applicator cup provided in accordance with the principles described herein, and that can provide an acceptable level of actinic radiation while the applicator cup is in contact with a stained tooth surface, would find utility in tooth whitening methods according to the present invention.

In general, the methods outlined herein seek to provide a biologically safe and effective level of actinic radiation to the surface of a patient's tooth, with each tooth being individually exposed to the optimal amount of light energy while simultaneously exposing the tooth surface to a tooth whitening composition. As a practical matter, however, variations in tooth sizes and shapes make it difficult to optimize treatment conditions for all teeth of every user. Nevertheless, an instrument embodying principles and concepts of the present invention enables a non-professional consumer to apply light of substantially uniform intensity to a tooth or tooth portion by directing onto the tooth surface being treated as much of the light emitted by the instrument as possible, while at the same time contacting the tooth surface with a tooth whitening composition. In a particularly advantageous embodiment described herein, this is achieved by providing an instrument having an applicator cup with a reservoir holding a whitening composition in contact with a tooth surface and being optically connected to one or more light outputs, whereby the reservoir is designed to serve as a spacing mechanism between a stained tooth surface and the one or more light outputs.

In that regard, the applicator cup and reservoir described above in connection with the illustrated embodiment of an instrument according to the invention, when positioned in proximity to the light output, will act as a spacer between the optical output and the tooth surface, with which it is in contact during use. Since the distance between the light output and the tooth surface is important to obtaining efficient use of light energy emitted by the light source, the reservoir should create a space between the optical output and the contacted tooth surface during use of not more than about 15 mm and preferably less than 10 mm. The size and shape of the open distal end of the reservoir is chosen consistent with the objects of the invention, but in general is preferably round and between about 3 mm to about 10 mm in diameter. Other shapes and sizes can also be used if found to be preferable for a given application. A preferred reservoir shape is a hollow circular cylinder with an internal transparent window element as described above, having a diameter of approximately 6 to 8 mm, a depth of approximately 1 to 3 mm, a flexible sleeve wall thickness of approximately 0.5 to 1.0 mm, and an internal volume (for containing the whitening composition) of approximately 100 cubic mm (0.1 cubic centimeters).

Compositions for Tooth Whitening Methods According to the Invention

Tooth whitening compositions suitable for use in tooth whitening methods performed using the instrument described above and shown in the drawings will be substantially transparent to the emitted actinic light, such that the light passes through both the reservoir and the whitening composition to reach the stained tooth surface without a significant reduction in light intensity. An example of a suitable composition for whitening a stained tooth surface includes an oxidizing compound such as a transparent 12% hydrogen peroxide gel with a pH of about 6.5 that has been thickened to approximately 70,000 cps with neutralized carboxypolymethylene.

The theoretical underpinning of the tooth bleaching methods described herein lies in the hypothesis that certain wavelengths of light are absorbed by tooth chromogens in a manner that promotes their oxidation to a non-chromogenic state. Reflectance studies show that dentin and enamel transmit green light, reflect yellow/red light and absorb blue light. Although not wishing to be bound by any particular theory, it appears that light is absorbed by the molecules responsible for tooth discoloration; thus, tooth chromogens may act in a manner similar to photosensitizers. In particular, exposure to certain wavelengths of actinic radiation may raise the energy state level of pi electrons carbonyl (C=O), double bond (C=C) and conjugated double bond (C=C—C=C) moieties, either changing their degree of unsaturation in the absence of an exogenously applied oxidizing agent, or alternatively making them more susceptible to attack by active oxidizing species such as perhydroxyl anion (HOO–), peroxyacid anions (RCOOO—), and radical species such as hydroxyl radical (HO*) and perhydroxyl radical (HOO*). In order to destroy or solubilize chromogenic substances, the activation energy of the reaction between one of the above light-absorbing moieties and an active oxidizing species must be overcome; thus, light-assisted chromogen attack leads to more efficient destruction of the molecular moieties responsible for the appearance of tooth discoloration by raising the energy state of electrons in specific chemical bonds within a light-absorbing molecule from a normal pi bonding orbital to a pi antibonding orbital. While in the less stable pi antibonding orbital, a light absorbing double bond has considerable single bond character and with sufficient light energy the conversion to a single bond becomes permanent. Alternatively, these destabilized double bonds are more easily attacked by oxidizing agents such as peroxides and peroxyacids. In theory, actinic light of a specific energy and wavelength, simply through the process described above, may utilize a tooth chromogen molecule as a photosensitizer in order to improve the efficacy of a given oxidative composition in contact with said tooth chromogen. However, given sufficient light energy with the correct wavelength, tooth stain chromogens may be rendered colorless simply through the direct process of photobleaching by actinic radiation.

Suitable tooth whitening compositions useful in the practice of the methods and procedures described herein may comprise one or more oxidizing agents selected from peroxides, peracids, and other oxidizing agents including but not limited to hydrogen peroxide, carbamide peroxide, peracetic acid, chlorine dioxide, sodium percarbonate, sodium perborate, calcium peroxide, and precursors or derivatives thereof. The one or more oxidizing agents may be included in the composition as a fully formed, reactive oxidizing agent, or alternatively may be provided in a multi-component form whereby prior to or during a tooth whitening procedure the multi-component composition is combined to form a single component composition and thereby form the active oxidizing agent or agents just prior to or during the procedure. Tooth whitening compositions useful in the practice of the present invention may also include one or more of the following: a thickening agent, a stabilizer, a flavorant, an accelerator, a surface active agent, a sweetener, a colorant, and an abrasive. Suitable tooth whitening compositions may have a viscosity in the range of 100 to 500,000 centipoise, and preferably between 1000 and 100,000 centipoise. Tooth whitening compositions useful with devices and instruments as described herein should be sufficiently transparent in order to transmit a desired percentage of the light energy emitted from the light emitting device (measured at a point just prior to the location at which the light impinges on the applicator cup reservoir). In the present description, the term "transparent" in this context means that the reservoir and the tooth whitening composition in situ therein transmit at least 25% of the emitted light energy, although it is more preferable that at least 50% of the emitted light energy is able to pass through the reservoir and composition, and it is most preferred that at least 75% of the emitted light energy is able to pass through the reservoir and composition.

EXAMPLES AND TEST RESULTS

The following examples and tests demonstrate the utility and efficacy of the present invention and the superior results it produces as compared to various known tooth whitening procedures. It will be understood that these examples do not limit the scope of the claimed subject matter, which is defined solely by the claims appended hereto.

Example 1

Measurement of Light Energy

This example reports the results of the measurement of the light energy emitted from an instrument with the salient features of the instrument 10 described above constructed in accordance with the above principles. As described above in connection with a preferred embodiment, the LED 110 of the instrument tested was a Luxeon® Rebel LXML-PR01-0500 royal blue light emitting diode (Philips Lumileds Lighting Co., San Jose, Calif.), with a nominal output rating of 500 milliwatts at 350 mA, that emits blue light comprising wavelengths between 400 nm and 500 nm, with a peak wavelength of approximately 455 nm. The light emitting surface of the LED was approximately 7 mm from the surface being treated, and the applicator cup 16 contained the transparent gel described in Example 2. The reservoir window 206 had a diameter of 8 mm, and the reservoir distal end 208 was spaced 2 mm from the window along the axis of the cylindrical sleeve 200. The flexible sleeve wall was about 1 mm thick and the reservoir had an internal volume of approximately 100 cubic mm (0.1 cubic centimeters).

The emitted light energy was measured using a Nova II laser power meter (Ophir-Spiricon LLC, North Logan, Utah). A low-power thermal sensor with a 17.5 mm aperture and a power range between 30 $mW/cm^2$ and 150 $W/cm^2$ (Ophir-Spiricon Model 30(150) A-BB-18 thermal sensor) was used to measure the power emitted by the device tested. The LED 110 of the device was positioned at the same distance (about 7 mm) from the sensor as would be anticipated for placement of the tooth whitening light in relation to the tooth surface(s) to be illuminated. Light intensity in milliwatts was recorded and converted into milliwatts (mW) per square centimeter ($cm^2$) as follows:

Light intensity($mW/cm^2$)=Meter reading(mW)/0.385 $cm^2$.

The light intensity provided by the tested instrument was calculated to be 250 $mW/cm^2$. Other tests using LEDs having performance specifications like those of LED 110 described above confirm that the wavelength of the light reaching the sensor would be between 400 nm and 500 nm, with a peak wavelength of approximately 455 nm. This instrument was used in the working examples described below. It had rechargeable batteries and a socket at the proximal end of the instrument that mounts on a battery charger base. In all of the tests reported below, the instrument batteries were kept fully charged by leaving the instrument on the battery charger base until use.

Example 2

Preparation of a Tooth Whitening Gel

A representative tooth whitening gel comprising hydrogen peroxide and having a transparency of 95% was prepared by combining the ingredients listed in Table 1 below in a vacuum mixer. The resulting gel was visually transparent and colorless, had a pH of approximately 6.5 when measured neat without dilution, and had a viscosity of approximately 70,000 centipoise. This gel was used in Examples 3 and 4 below to demonstrate the tooth whitening ability and/or enhancement provided by employing principles of the present invention.

TABLE 1

| Ingredient | Percent (wt.) |
| --- | --- |
| Deionzied water | 57.300 |
| Glycerin | 20.000 |
| 1-hydroxyethylidine-1,1-diphosphonic acid | 0.500 |
| Potassium stannate | 0.100 |
| Sodium saccharin | 0.600 |
| Hydrogen peroxide | 12.000 |
| Carbopol 974P | 3.000 |
| PEG-60 hydrogenated castor oil | 3.000 |
| Flavor | 1.000 |
| Ammonium hydroxide (29% solution) | 2.500 |
| Total | 100.000 |

Example 3

Comparative Removal of Tooth Stains in an In Vitro Model

In accordance with a commonly used technique for in vitro testing of tooth whitening compositions, this example used a series of stained bovine enamel slabs to test the efficacy of the light-emitting instrument 10 described in Example 1 above using the tooth whitening gel composition described in Example 2 in removing or destroying stains on tooth enamel. Slabs providing a Control baseline were contacted with a non-active tooth whitening composition (the composition of Example 2 without hydrogen peroxide). A second set of slabs was contacted with the tooth whitening gel of Example 2 alone, but without exposure to light. A third set of slabs (referred to in Table 2 below as "Gel+Light") was treated with tooth whitening gel of Example 2 using the instrument described in Example 1 to apply light energy through the tooth whitening composition contained in the applicator cup 16 of the instrument. The treatment time for each test slab was 30 minutes, after which the slabs were rinsed and measured for L*a*b* values as described further below.

Each series of tests as described above was performed on three unsealed 10 mm×10 mm bovine incisor (enamel) slabs having a 600 grit finish and mounted in clear resin, prepared in accordance with the following protocol:

1. Storage of substrates
   Store substrates (bovine incisor enamel fragments) at 100% relative humidity, or at 4° C. in ddH$_2$O or a phosphate buffer saline (PBS) solution having a pH of 7.4 with one of the compositions shown in the following table (substrates should not be permitted to fully dry to avoid surface change):

| Salt | Concentration (mmol/L) | Concentration (g/L) |
| --- | --- | --- |
| NaCl | 137 | 8.00 |
| KCl | 2.7 | 0.20 |
| Na$_2$PO$_4$ | 10 | 1.44 |
| KH$_2$PO$_4$ | 1.76 | 0.24 |

2. Staining broth
   a. 3 g of fine ground leaf Tea
   b. 3 g of fine ground Coffee
   c. 300 ml of boiling ddH$_2$O
   d. Infuse for 10 min with stirring (using magnetic stirrer)
   e. Filter solution through tea strainer with additional filter paper
   f. Cool to 37° C.
3. Preparation of samples
   a. Number the samples on one side of the resin with permanent marker (to track the samples if more than one)
   b. Rub the surface of the enamel with wet wipe and then grit finish on the wet surface with orbital motion covering the whole surface for nearly 10 sec
   c. Wash the surface with water and dry with a tissue
   d. Seal all the surfaces of the resin, excluding the enamel surface of bovine fragment (i.e., all four sides and bottom) with clear nail varnish
   e. Leave it on bench top for air drying
   f. Etching: sequential immersion in 0.2M HCl, saturated N$_2$CO$_3$, 1% Phytic acid, and finally rinse with ddH$_2$O
   g. Dry with tissue—samples are ready for staining
4. L*a*b measurement (before and after staining)
   a. Use Konica-Minolta CM-700d Spectrophotometer with 3 mm aperture for L*a*b measurements
   b. Power up control unit (connected to device)
   c. Select "Calibrate" and allow to load
   d. Place calibration tile over device aperture—select "Measure"
   e. Device is ready to measure substrates
   f. Rinse substrates with ddH$_2$O, blot surface dry with tissue
   g. Place substrate enamel side down over device aperture with substrate number right way up (i.e., the numeral of substrate "1" should be upright, not at 90° or otherwise)
   h. Measure L*a*b by selecting "Measure"
   i. Turn substrate 90° clockwise—measure L*a*b (see below)
   j. Repeat 3 times until substrate has been measured at four orientations
   k. Place substrate back in storage until treatment/de-staining, etc.
5. Staining
   a. Prepare the staining broth (per section 2) and fill a glass bottle with 200 ml of the broth
   b. Keep the samples to be stained in the broth continuously for four days
   c. Tighten the cap of the bottle to ensure that the broth does not evaporate from the bottle
   d. Gently mix the broth every day to make sure that the particles are not settling at the bottom of the bottle
   e. After staining the samples, rinse substrate with Millipore water, dry with a tissue and measure L*a*b values Test Results The L*a*b* values of each of the stained bovine enamel slabs prepared and tested as described above were recorded before and after treatment as shown in the table below. The net change in color delta E (ΔE) of each slab was calculated in the conventional fashion as follows:

$$\Delta E=(\Delta L^2+\Delta a^2+\Delta b^2)^{1/2}$$

The ΔE number reflects the net change in distance moved within a 3-dimensional color space and is commonly used to numerically communicate the improvement in tooth color shown in teeth whitening clinical studies, both in vitro and in vivo. The average value of ΔE for each set of slabs was calculated and is reported in the following Table 2. In general, the higher the ΔE value, the better the whitening effect.

TABLE 2

| Tested | Initial | | | After 30 Minutes | | | Change |
|---|---|---|---|---|---|---|---|
| | L | a | b | L | a | b | ΔE |
| Control | 64.33 | 4.11 | 18.32 | 64.99 | 4.18 | 18.11 | 0.70 |
| Gel Only | 64.33 | 6.08 | 23.60 | 66.50 | 3.89 | 18.43 | 6.02 |
| Gel + Light | 65.90 | 4.00 | 19.87 | 72.72 | 1.54 | 4.98 | 16.56 |

As can be seen by the stark differences in the ΔE color changes between the Control, Gel Only and Gel+Light groups, the combination of Gel+Light in accordance with principles of the present invention leads to a superior degree of whitening compared to the other groups.

Example 4

Comparative Removal of Stains In Vivo

Six volunteers were selected who had sufficiently stained teeth (A3 or higher on the VITA® Shade Guide described above) to be good candidates for tooth whitening. Each subject was instructed in an office setting on how to apply the tooth whitening gel of Example 2 into the applicator cup 16 of the light-applying instrument described in Example 1 above and how to use the instrument in accordance with the procedures described herein. That is, the subjects were instructed to use the instrument for 10 minutes twice daily, contacting each of the 16 tooth surfaces within the smile line (the teeth that are typically visible when an individual smiles, comprising the eight central teeth on top and the eight central teeth on the bottom) for at least a total of 40 seconds each day. Subjects' starting tooth shade was recorded before departing the office with the instrument and sufficient gel (as described above in Example 2) for treatment for seven days, and they were asked to record any difference they noticed in color change.

At the end of the seven day test period, all of the volunteers reported noticing whiter teeth after the first ten minute application. The average shade change for the six subjects was six shades, with the lowest change being four shades and the highest change being ten shades. The instrument and the procedure were well accepted by all study participants, and none reported tooth or gum irritation or sensitivity.

Example 5

In Vitro Study of Antimicrobial Effect of Light-Emitting Instrument

A Time Kill Test provided an in vitro method for demonstrating the antimicrobial activity of the LED light-emitting instrument described in Example 1 above. The test organisms were *Fusobacterium nucleatum* ATCC 10953 and *Porphyromonas gingivalis* ATCC 33277. As discussed in more detail below, testing was performed in triplicate with plating in duplicate.

The following reagents, equipment, and supplies were used to perform these tests:
1. Dilution fluid-sterile phosphate buffered saline (PBS) or equivalent (neutralizers can be added if required)
2. Tryptic soy agar (TSA)
3. Schaedler Blood Agar (SBA) (5% sheep blood with vitamin K and hemin)
4. Sterile bacteriological pipettes
5. Sterile Petri dishes
6. Sterile test tubes
7. Sterile white Nunc® MicroWell® 96-well plates
8. Laboratory supplies, e.g. test tube racks, glassware, forceps, pipettes, etc.
9. Incubator (36-38° C., or temperature necessary for growth of test organisms)
10. Anaerobic chamber or container
11. Timer (displaying seconds)
12. Colony counter
13. Sterilizer
14. Vortex mixer
15. Magnetic stirring mixer
16. Blue-light filtering safety glasses
17. Ophir-Spiricon Nova II laser power meter
18. Ophir-Spiricon Model 30(150)A-BB-18 medium power thermal sensor
19. Custom white HDPE insert plug for sensor with geometry to match wells in 7 above.

Time Kill Tests

Inoculum Preparation for the Time Kill Tests.

Microorganism culture(s) were transferred twice (once every 48 to 72 hours or as appropriate for a given test organism) on Schaedler Blood Agar or other appropriate growth media and incubated anaerobically at 37.0±2.0° C. (or temperature as appropriate for a given test organism). The second transfer was made onto an agar plate or slant and the inoculum prepared by washing the plate or slant with 5-10 ml of sterile PBS or sterile saline.

Suspensions of all organisms were poured into an appropriate size sterile tube and centrifuged at approximately 4,000 rpm for about 10 minutes. The supernatant was decanted, and the pellet resuspended by vortexing in 5-10 ml of PBS or sterile saline. The concentration of test organisms will be adjusted spectrophotometrically in PBS to a concentration of approximately $1\times10^8$ CFU/ml.

Inoculum Enumeration.

Aliquots containing $10^{-5}$ and $10^{-6}$ organisms were plated in triplicate, and plates were spread onto Schaedler Blood Agar. The plates were incubated anaerobically at 37.0±2.0° C. (or temperature as appropriate for a given test organism) for a minimum of 72 hours, and the colonies were counted and recorded as CFU/mL. If the test period ran longer than 60 minutes, the enumeration series of plates was repeated and each series of plates identified as either a "pre-test" or "post-test" count. To be valid, the beginning and end counts had to be within one $\log_{10}$.

Time Kill Procedure.

200 μL of each test organism were inoculated into separate wells of a sterile White Nunc® MicroWell® 96-well plate to achieve approximately between 105-106 CFU/mL per well. A total of nine wells were inoculated into one plate for each test organism. There were two empty wells spaced between each replicate. This prevented the organism wells from being exposed to stray light exposure from the test instrument. Control test organisms (without exposure to light) were inoculated on a separate plate and sampled at time zero and served as the initial inoculum count.

Exposure of Test Organisms to LED Light.

As noted above, the instrument was kept in the charging socket between each test procedure to ensure that the batteries were fully charged. The first three wells were exposed to the test article by placing the rim 208 of an empty applicator cup 16 (that is, without a whitening composition therein) over the center of each well and flush with the top of the well. The test instrument LED was turned on and the test organism wells were exposed to light for 15 seconds for each set of three separate wells (A, B, and C). After each 15 second exposure, 0.1 mL (100 µL) was removed and inoculated into 9.9 mL sterile saline blank). The process was repeated with three separate wells for 30 seconds exposure and another three separate wells for 60 seconds exposure.

A serial ten-fold dilution was performed in sterile saline of each replicate to $10^{-5}$. Plate 0.1 mL dilutions were spread onto duplicate plates of Schaedler Blood Agar for each replicate, and incubated anaerobically at 37.0±2.0° C. for at least 72 hours. Plates with ≤250 colonies per plate were removed and the number of colonies was counted.

Test Results

Results are tabulated below in Tables 3 and 4 in terms of the number of surviving organisms over time for each of the microorganisms tested. Plates containing ≤250 colonies per plate were used for calculations where possible. The number of surviving organisms at a particular time was determined by averaging the plate counts, correcting for dilution, and log transforming this corrected value (see below). This log transformed value was expressed as the result. Reduction in counts after exposure to test material compared to the blank indicated the efficacy of the test device.

TABLE 3

*Fusobacterium nucleatum* ATCC 10953

| | Contact time t (in seconds) | | | |
|---|---|---|---|---|
| | t = 0 (control) | t = 15 | t = 30 | t = 60 |
| Well A | $1.7 \times 10^6$ | <100 | <100 | <100 |
| Well B | $1.7 \times 10^6$ | <100 | <100 | <100 |
| Well C | $1.7 \times 10^6$ | <100 | <100 | <100 |
| Average count | $1.7 \times 10^6$ | <100 | <100 | <100 |
| $Log_{10}$ average | 6.23 | <2 | <2 | <2 |
| $Log_{10}$ reduction* | Not applicable | >4.23 | >4.23 | >4.23 |
| % reduction* | Not applicable | >99.99 | >99.99 | >99.99 |

TABLE 4

*Porphyromonas gingivalis* ATCC 33277

| | Contact time t (in seconds) | | | |
|---|---|---|---|---|
| | t = 0 (control) | t = 15 | t = 30 | t = 60 |
| Well A | $1.8 \times 10^6$ | <100 | <100 | <100 |
| Well B | $1.9 \times 10^6$ | <100 | <100 | <100 |
| Well C | $1.9 \times 10^6$ | <100 | <100 | <100 |
| Average count | $1.9 \times 10^6$ | <100 | <100 | <100 |
| $Log_{10}$ average | 6.23 | <2 | <2 | <2 |
| $Log_{10}$ reduction* | Not applicable | >4.28 | >4.28 | >4.28 |
| % reduction* | Not applicable | >99.99 | >99.99 | >99.99 |

*Percent reduction = A/B × 100, where
A = (Initial CFU Recovered Unexposed Control) − (Final CFU after Exposure to Light for 15, 30, and 60 sec)
B = Initial CFU Recovered Unexposed Control
Log reduction = $Log_{10}A - Log_{10}B$

CONCLUSION

It will be understood that the embodiments of the invention described above can be modified in myriad ways other than those specifically discussed without departing from the scope of the invention. For example, in addition to tooth whitening, other dentally therapeutic functions can be served by apparatus and methods according to the present invention. Specific examples are delivery of anticaries, antiplaque, and antimicrobial compositions to the teeth and gum surfaces. Both human and non-human (for example, pets) are potential subjects for cosmetic and/or therapeutic treatment using the present invention, and apparatus and methods according to the invention can be used to deliver topically active substances to one or more skin surface targets, to affect an anti-aging, anti-acne, or other cosmetic and/or therapeutic dermatological functions.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A dental instrument for use by a non-professional to whiten teeth by applying a tooth whitening composition to a tooth surface while exposing the tooth surface to actinic radiation within a predetermined range of wavelengths, the instrument comprising:

an instrument body with a mounting boss for accepting a container with a reservoir holding a tooth whitening composition, the instrument body including a handle for the user to position an open end of the reservoir in contact with a tooth surface of the user and a neck portion pivotally attached to the handle with the mounting boss at a distal end of the neck portion;

an actinic radiation source within the instrument body for emitting actinic radiation within a predetermined range of wavelengths through a window in the container and tooth whitening composition in the reservoir without substantially attenuating the intensity of the actinic radiation emitted by the radiation source;

a safety cut-out for terminating power to the actinic radiation source unless a predetermined force is applied to the distal end of the neck portion in a direction that holds the open end of the reservoir in contact with a tooth surface;

a vibrational motor that imparts vibration to the container; and a user-operated main ON/OFF switch for placing the instrument in an ON state that connects a source of electrical power to the actinic radiation source and the vibrational motor, wherein:

the safety cut-out includes a safety switch operated by pivoting movement of the neck portion relative to the handle and a spring biasing the neck portion into a position maintaining the safety switch in an open state wherein power is not supplied to the actinic radiation source, the safety switch is placed in a closed state when the neck portion is pivoted about the handle in the direction that holds the open end of the reservoir in contact with the tooth surface, power is supplied to the actinic radiation source when the instrument is in the ON state only if the safety switch is closed, and power is supplied to the vibrational motor when the instrument is in the ON state and the safety switch is in the open state.

2. A kit comprising a dental instrument as in claim 1 and a container for the tooth whitening composition, the container including:
   a hollow, rigid cylindrical container body having a proximal end with a mount for removably attaching the container body to the mounting boss of the dental instrument;
   a window member spaced from the proximal end of the container body in the path of the actinic radiation from the dental instrument, the window member being substantially transparent to the actinic radiation; and
   a hollow, flexible cylindrical sleeve connected to the container body and extending to a distal end spaced from the proximal end of the container body, wherein the reservoir is formed by the sleeve and the window member, and the open end of the reservoir is formed by a flexible rim at the distal end of the sleeve for promoting sealing contact between the sleeve and tooth surface.

3. A kit as in claim 2, wherein the window member permits at least 25% of actinic light comprising wavelengths between 400 nm to 700 nm to pass therethrough.

4. A kit as in claim 2, wherein:
   the container body is substantially circular in transverse cross section and the body and the window member comprise a single piece molded from a plastic resin unit with the window member forming a closed end of the reservoir; and
   the flexible sleeve is substantially circular in transverse cross section and comprises a single piece molded in place on the container body with at least a portion of the sleeve overlapping an outside surface of the container body.

5. A kit as in claim 2, wherein the sleeve substantially covers the entire outside surface of the container body and is substantially opaque to the actinic radiation.

6. A kit as in claim 5, wherein the sleeve comprises an elastomer that is impermeable to the tooth whitening composition.

7. A kit as in claim 5, wherein:
   a proximal end of the sleeve extends beyond a proximal end of the container body; and
   the mount causes the proximal end of the sleeve to be compressed against a surface of the dental instrument to form a seal therewith when the container body is attached to the instrument.

8. A kit as in claim 2, wherein the container further includes a tooth whitening composition in the reservoir and a removable film adhered to the distal rim of the sleeve to seal the reservoir with the tooth whitening composition therein.

9. A kit as in claim 8, further comprising a plurality of the containers, each container including the tooth whitening composition in the reservoir and a removable film adhered to a distal rim of the sleeve to seal the reservoir with the tooth whitening composition therein.

10. A kit as in claim 2, wherein the container body consists of a material selected from polycarbonate/acrylonitrile butadiene styrene, polystyrene, and clarified polypropylene, and the sleeve consists of a thermoplastic elastomer.

11. An instrument as in claim 1, wherein the actinic radiation source comprises an LED emitting visible light comprising wavelengths between about 400 nm and 700 nm.

12. An instrument as in claim 11, wherein the distance from the light emitting surface of the LED to the open end of the reservoir is between about 10 mm and 15 mm.

13. An instrument as in claim 1, wherein the light intensity at the open end of the reservoir is at least about 100 milliwatts per square centimeter.

14. A dental instrument for applying a tooth whitening composition to a tooth surface while exposing the tooth surface to actinic radiation, the instrument comprising: an instrument body including a handle for a user and a neck portion movably attached to the handle, wherein the neck portion includes mounting structure for accepting a container holding a tooth whitening composition, the neck portion being movably mounted to the handle at a location that enables the user to contact a tooth surface in an oral cavity with tooth whitening composition in the container;
   an actinic radiation source within the instrument body for emitting actinic radiation through a window in the container and tooth whitening composition therein;
   a safety cut-out for terminating power to the actinic radiation source unless a predetermined force is applied to the neck portion in a direction that holds tooth whitening composition in the container in contact with a tooth surface;
   a vibrational motor that imparts vibration to the container; and
   a user-operated main ON/OFF switch for placing the instrument in an ON state that connects a source of electrical power to the actinic radiation source and the vibrational motor, wherein:
      the safety cut-out includes a safety switch operated by movement of the neck portion relative to the handle and a spring biasing the neck portion into a position maintaining the safety switch in an open state wherein power is not supplied to the actinic radiation source,
      the safety switch is placed in a closed state when the neck portion is moved relative to the handle in a direction that holds tooth whitening composition in the container in contact with the tooth surface,
      power is supplied to the actinic radiation source when the instrument is in the ON state only if the safety switch is closed, and
      power is supplied to the vibrational motor when the instrument is in the ON state and the safety switch is in the open state.

15. A kit comprising a dental instrument as in claim 14 and a container for the tooth whitening composition, the container including:
   a hollow, rigid cylindrical container body having a proximal end with a mount for removably attaching the container body to the mounting structure of the dental instrument;
   a window member spaced from the proximal end of the container body in the path of the actinic radiation from the dental instrument, the window member being substantially transparent to the actinic radiation; and
   a hollow, flexible cylindrical sleeve connected to the container body and extending to a distal end spaced from the proximal end of the container body, wherein the reservoir is formed by the sleeve and the window member, and an open end of the reservoir for contacting the tooth whitening composition with the tooth surface is formed by a flexible rim at the distal end of the sleeve for promoting sealing contact between the sleeve and tooth surface.

16. A kit as in claim 15, wherein:
   the container body is substantially circular in transverse cross section and the body and the window member comprise a single piece molded from a plastic resin unit with the window member forming a closed end of the reservoir; and the flexible sleeve is substantially circular in transverse cross section and comprises a single piece molded in place on the container body with at least a portion of the sleeve overlapping an outside surface of the container body; and the sleeve substantially covers the entire outside surface of the container body and comprises an elastomer that is substantially opaque to the actinic radiation and impermeable to the tooth whitening composition.

17. A kit as in claim 16, wherein:

a proximal end of the sleeve extends beyond a proximal end of the container body; and the mount causes the proximal end of the sleeve to be compressed against a surface of the dental instrument to form a seal therewith when the container body is attached to the instrument.

18. A kit as in claim 15, wherein the container further includes a tooth whitening composition in the reservoir and a removable film adhered to the distal rim of the sleeve to seal the reservoir with the tooth whitening composition therein.

19. A kit as in claim 15, wherein the container body consists of a material selected from polycarbonate/acrylonitrile butadiene styrene, polystyrene, and clarified polypropylene, and the sleeve consists of a thermoplastic elastomer.

20. An instrument as in claim 14, wherein the actinic radiation source comprises an LED emitting visible light comprising wavelengths between about 400 nm and 700 nm.

21. An instrument as in claim 20, wherein the distance from the light emitting surface of the LED to the open end of the reservoir is between about 10 mm and 15 mm.

* * * * *